United States Patent [19]

Hessler et al.

[11] 4,216,159

[45] Aug. 5, 1980

[54] SYNTHESIS OF 16-UNSATURATED PREGNANES FROM 17-KETO STEROIDS

[75] Inventors: Edward J. Hessler, Kalamazoo; Verlan H. Van Rheenen, Portage, both of Mich.

[73] Assignee: The Upjohn Company, Kalamazoo, Mich.

[21] Appl. No.: 909,349

[22] Filed: May 25, 1978

[51] Int. Cl.$^2$ .............................. C07J 9/00; C07J 1/00
[52] U.S. Cl. ............................ 260/397.1; 260/239.5; 260/239.55 C; 260/397.45; 260/397.5; 260/397.4
[58] Field of Search ............... 260/239.5, 397.1, 397.4, 260/397.45

[56] References Cited

U.S. PATENT DOCUMENTS

| | | | |
|---|---|---|---|
| 3,281,415 | 10/1966 | Schneider et al. | 260/239.55 |
| 3,493,563 | 3/1970 | Diassi | 260/239.55 |
| 3,541,082 | 11/1970 | Huber | 260/239.55 |
| 3,631,076 | 12/1971 | Clark et al. | 260/397.45 |
| 3,839,369 | 10/1974 | Hofmeister et al. | 260/239.55 |
| 4,041,055 | 8/1977 | Shepard et al. | 260/397.3 |
| 4,076,737 | 2/1978 | Anner et al. | 260/397.45 |
| 4,089,852 | 5/1978 | Nickolson et al. | 260/397.47 |

FOREIGN PATENT DOCUMENTS

| | | | |
|---|---|---|---|
| 2521231 | 11/1976 | Fed. Rep. of Germany | 260/397.47 |
| 2603266 | 8/1977 | Fed. Rep. of Germany | 260/397.47 |

OTHER PUBLICATIONS

J. Org. Chemistry, Apr. 14, 1978 article by Ham et al. pp. 1595–1597.
Tetrahedron Letters (1968) No. 8, p. 937.

*Primary Examiner*—Elbert L. Roberts
*Attorney, Agent, or Firm*—Bruce Stein

[57] ABSTRACT

17-Keto steroids (I) in their protected form (IIa or IIb) are reacted with a metalated olefin (VI) to give a 21-aldehyde (IV) which is readily transformed to a 16-unsaturated pregnane (V) which is useful in the production of commercially important substituted corticoids.

118 Claims, No Drawings

SYNTHESIS OF 16-UNSATURATED PREGNANES FROM 17-KETO STEROIDS

BACKGROUND OF THE INVENTION

Various processes are known for the production of 21-hydroxypregna-4,16-diene-3,20-diones.

U.S. Pat. No. 3,839,369 claims a process for preparing a 21-hydroxypregna-4,9(11),16-triene-3,20-dione-type steroid by heating the corresponding 17-nitrate ester. The present invention does not go thru a 17α-hydroxy steroid or involve a nitrate ester.

U.S. Pat. No. 3,493,563 discloses a process for preparing a 21-hydroxypregna-4,9(11),16-triene-3,20-dione-type steroid by dehydrating with thionyl chloride or phosphorus oxychloride the corresponding 17α,21-dihydroxy-20-keto steroid. The process of the present invention introduces the double bond at C-16 during the addition of the two carbon side chain at C-17 starting with an androstenedione-type steroid.

U.S. Pat. No. 3,631,076 claims a process for preparing a 16-unsaturated steroid by reacting a 17α-alkanoyloxy or 17-aroyloxy corticoid with an alkali metal or alkaline earth metal salt of a lower alkanoic or aromatic acid. The process of the present invention does not produce or proceed thru a corticoid but produces the 16-unsaturated steroid from a 17(20)-unsaturated-21-aldehyde (IV).

U.S. Pat. Nos. 3,281,415 and 3,541,082 disclose processes to produce $\Delta^{16}$-pregnanes from C-20 hydroperoxides which are produced by photosensitized oxidation of the corresponding $\Delta^{17(20)}$-steroidal olefins. The present invention involves neither photosensitized oxidation nor hydroperoxides.

German Offenlegungsschrift No. 2,603,266 discloses a process for adding the 21-hydroxy-20-keto side chain to a 17-keto steroid. The process does not proceed along the synthetic pathway of the present invention, nor does it produce the 21-aldehyde (IV) intermediate or the C-16 unsaturated compounds of the present invention.

U.S. Pat. No. 4,041,055 claims a process for adding a 2 carbon side chain to a 17-keto steroid via ethisterone-type compounds and does not produce C-16 unsaturated compounds.

J. Ficini et al. in Tetrahedron Letters 8, 937 (1968) describe the synthesis of various lithium chlorovinyl ethers and the reactions of lithiated cis-2-chloro-1-ethoxyethylene with cyclohexanone to give an α,β-unsaturated α-chloroaldehyde. The yield quoted was about 40%, see page 940. When ketones are reacted with strongly basic compounds such as the lithium compounds of Ficini a significant amount of enolization of the ketone is expected and therefore upon work up a significant amount of starting material is regenerated which should significantly reduce the yield. Therefore, the low yield, about 40% obtained by Ficini is expected. Surprisingly and unexpectedly when either trans-2-chloro-2-lithio-1-ethoxyethylene (VIb) or the cis-trans mixture (VIa and VIb) is added to the protected 17-keto steroid (IIa or IIb) the α,β-unsaturated α-chloroaldehyde (IV) is produced in about 90% yield. This is all the more surprising and unexpected because Ficini uses a six member cyclic ketone (cyclohexanone) where less enolization is expected than with the five member cyclic ketones of the protected 17-keto steroids (IIa or IIb).

German Offen. No. 2,521,231 discloses a process of reacting a 17-keto steroid with a lithiated cis-2-alkoxy-1-alkoxyethylene to form a 17β-hydroxy-20,21-dialkoxy-20-unsaturated steroid which is subsequently converted to a 21-alkoxy-$\Delta^{16}$-20-keto steroid.

K. S. Y. Lau et al., J. Org. Chem. 43, 1595 (1978), describe the reaction of cis and trans 2-bromo-1-ethoxyethylene with butyl lithium and the subsequent reaction of the lithiated vinyl ether with a ketone to give an α,β-unsaturated aldehyde. When the cis 2-bromo-1-ethoxyethylene was reacted with butyl lithium, the lithium exchanged with the bromine forming 2-lithio-1-ethoxyethylene. When Lau et al. reacted trans 2-bromo-1-ethoxyethylene with butyl lithium, the lithium exchanged with a proton and formed 2-lithio-2-bromo-1-ethoxyethylene. When Lau et al. reacted this halogenated vinyl ether with cyclopentanone, they obtained the α-halogenated α,β-unsaturated aldehyde in 30% yield. In the present invention when cis 2-chloro-1-ethoxyethylene is reacted with butyl lithium the lithium exchanges not with the halogen but with a proton forming 2-lithio-2-chloro-1-ethoxyethylene which when reacted with a 17-keto steroid produces an α-halogenated α,β-unsaturated aldehyde. While Lau's process using the cis brominated vinyl ether will not produce any α-halogenated α,β-unsaturated aldehyde, the process of the present invention using the corresponding cis chlorinated vinyl ether produces the α-chlorinated α,β-unsaturated aldehyde in about 50% yield. While Lau's process using the trans isomer produced the α-halogenated α,β-unsaturated aldehyde in only 30% yield, the process of the present invention using trans 2-chloro-1-ethoxyethylene surprisingly and unexpectedly produces the halogenated α,β-unsaturated aldehyde (IV) in 91.2% yield (Example 1).

SUMMARY OF THE INVENTION

Disclosed is a process for the preparation of a compound of the formula:

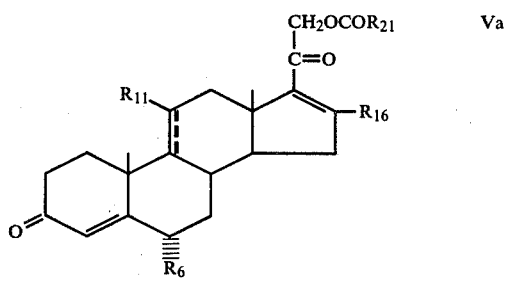

which comprises
(1) reacting a compound of the formula:

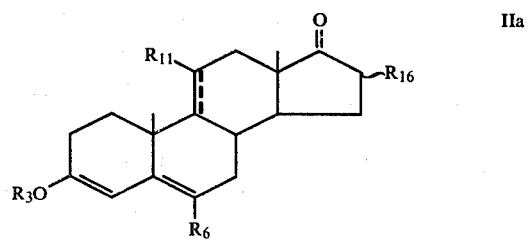

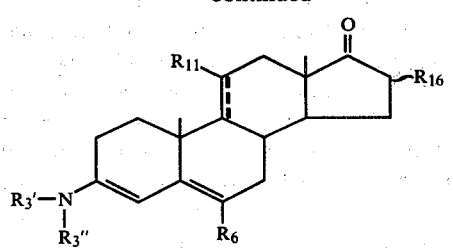

IIb

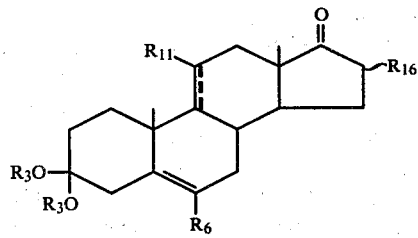

IIc with a metalated olefin selected from the group consisting of a cis-trans mixture (VIa and VIb) or trans (VIb) compounds of the formula:

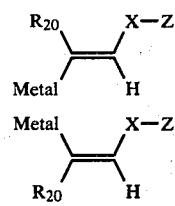 VIa

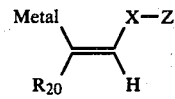 VIb (2) acid hydrolysis and (3) reaction with a compound of the formula $R_{21}CO_2^{\ominus}$ in an aprotic diluent.

Also disclosed is a process for the preparation of both geometrical isomers at $C_{20}$ of a compound of the formula:

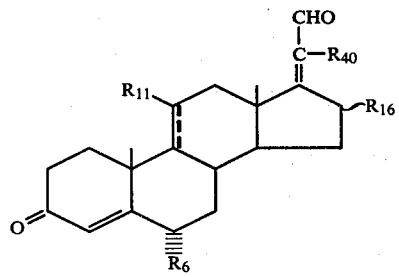 IVa which comprises (1) reacting a compound of formula (IIa, IIb or IIc) with a metalated olefin selected from the group consisting of a cis-trans mixture (VIa and VIb) or trans (VIb) and (2) acid hydrolysis.

Further disclosed is a process for the preparation of a compound

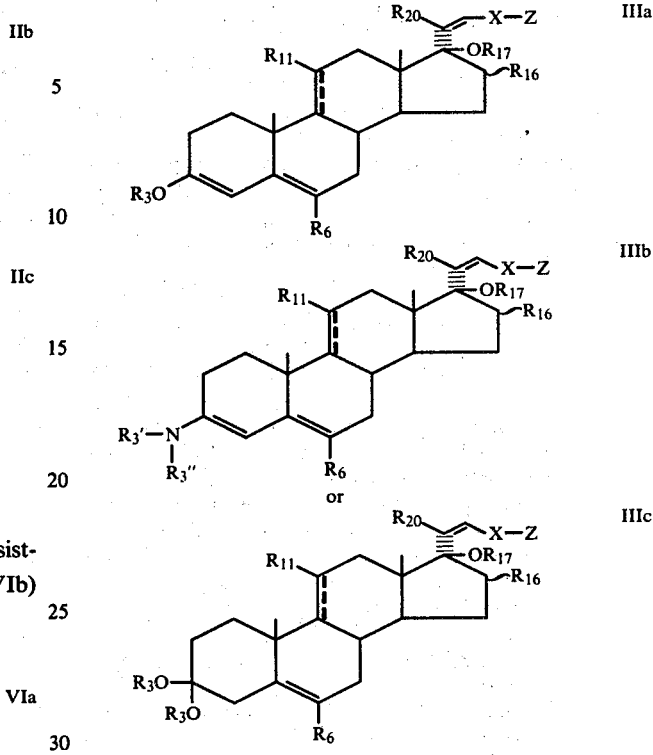

and the cis $C_{20\text{-}21}$ isomer thereof which comprises (1) reacting the corresponding $C_3$ protected compound of formula (IIa, IIb or IIc) with a metalated olefin selected from the group consisting of a cis-trans mixture (VIa and VIb) or trans (VIb) and (2) quenching the reaction with a compound of the formula $R_{17a}$-W, $(R_{17a}CO)_2O$, $R_{17a}COM$ or water.

Additionally disclosed is a process for the preparation of a compound of formula (IVa) which comprises acid hydrolysis of a compound of formula (IIIa, IIIb or IIIc).

Disclosed is a process for the preparation of a compound of the formula:

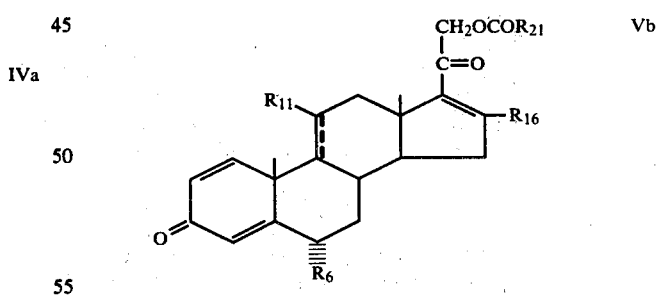 Vb which comprises (1) reacting a compound of the formula:

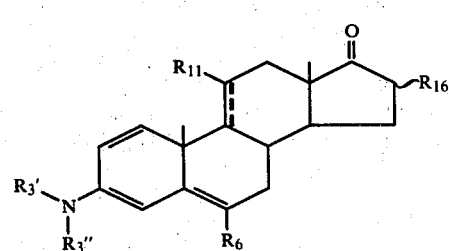 IId

-continued

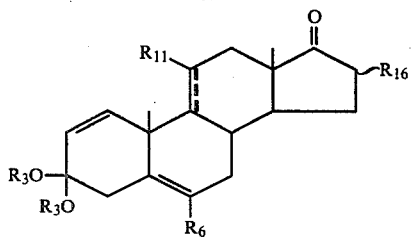

IIe with a metalated olefin selected from the group consisting of a cis-trans mixture (VIa and VIb) or trans (VIb)
(2) acid hydrolysis and
(3) reaction with a compound of the formula $R_{21}CO_2^{\ominus}$ in an aprotic diluent.

Also disclosed is a process for the preparation of both geometrical isomers at $C_{20}$ of a compound of the formula:

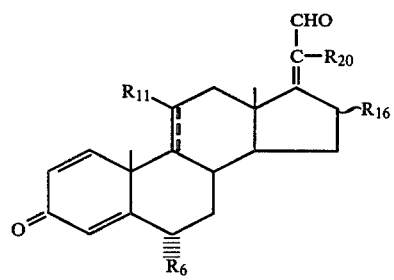

IVb which comprises
(1) reacting a compound of formula (IId or IIe) with a metalated olefin selected from the group consisting of a cis-trans mixture (VIa and VIb) or trans (VIb) and
(2) acid hydrolysis.

Further disclosed is a process for the preparation of a compound of formula:

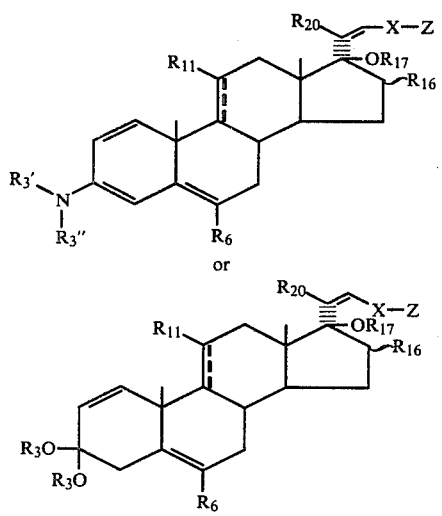

IIId or

IIIe and the cis $C_{20\text{-}21}$ isomer thereof which comprises
(1) reacting the corresponding $C_3$ protected compound of formula (IId or IIe) with a metalated olefin selected from the group consisting of a cis-trans mixture (VIa and VIb) or trans (VIb) and (2) quenching the reaction with a compound of the formula $R_{17a}\text{-W}$, $(R_{17a}CO)_2O$, $R_{17a}COM$ or water.

Additionally disclosed is a process for the preparation of a compound of formula (IVb) which comprises acid hydrolysis of a compound of formula (IIId or IIIe).

Disclosed is a process for the preparation of a compound of the formula:

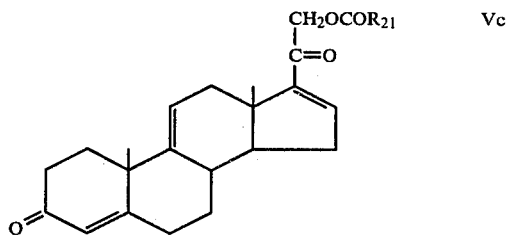

Vc which comprises reacting 20-bromopregna-4,9(11),17(20)-trien-3-one-21-al with a compound of the formula $R_{21}CO_2^{\ominus}$ in an aprotic diluent.

Also disclosed is a process for the preparation of a compound of formula:

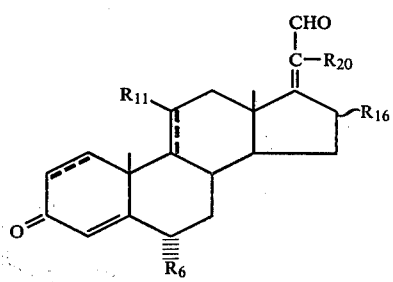

V which comprises reacting a compound of the formula:

IV with a compound of the formula $R_{21}CO_2^{\ominus}$ in an aprotic diluent.

Also disclosed are compounds of formulas IV, IIIa, IIIb, IIIc, IIId, IIIe, IIIf and IIIg.

Disclosed is 20-bromopregna-4,9(11),17(20)-trien-3-one-21-al.

DETAILED DESCRIPTION OF THE INVENTION

The 17-keto steroid (I) starting materials are well known to those skilled in the art or may readily be prepared from known compounds by methods well known to those skilled in the art. For example, the $\Delta^{1,4}$-17-keto steroids (I) are known, see U.S. Pat. No. 2,902,410, in particular Example 1. The $\Delta^{4,9(11)}$-17-keto steroids (I) are known, see U.S. Pat. No. 3,441,559, in particular Example 1. The 6α-fluoro-17-keto steroids (I) are known, see U.S. Pat. No. 2,838,492, in particular Examples 9 and 10. The 6α-methyl-17-keto steroids (I) are known, see U.S. Pat. No. 3,166,551 in particular Example 8.
The 16β-methyl-17-keto steroids (I) can readily be prepared from the corresponding 17-keto steroid (I) by the processes of U.S. Pat. Nos. 3,391,169 (Examples 75, 76), 3,704,253 (column 2 and Examples 1–3) and 3,275,666.
Chart A discloses the process of the present invention. The 17-keto steroids (I)
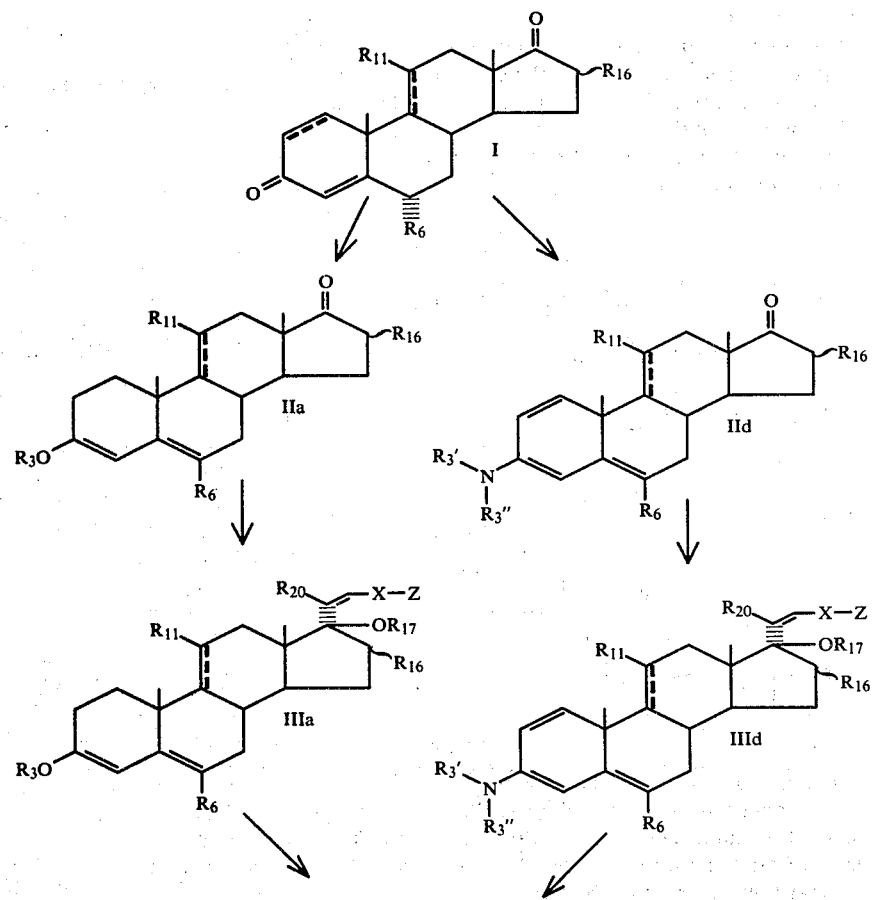
CHART A

CHART A

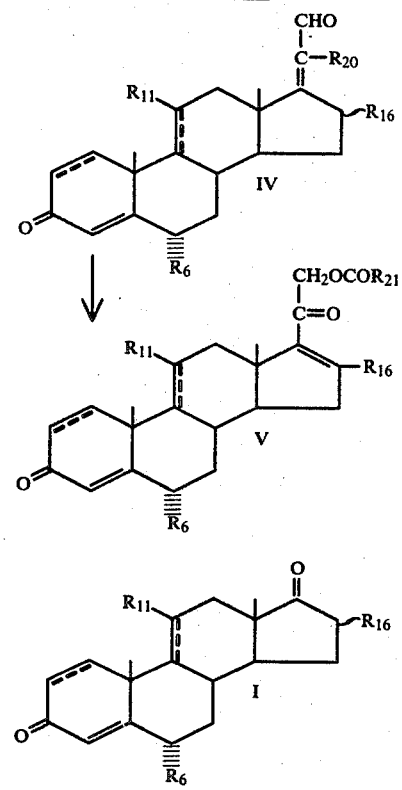

where $R_6$ is a hydrogen or fluorine atom or methyl group; where $R_{11}$ is a hydrogen atom, $\alpha$-$OR_{11a}$ or $\beta$-$OR_{11a}$; where $R_{11a}$ is a hydrogen atom or TMS with the proviso that when $R_{11}$ is —$OR_{11a}$, $\rightleftharpoons$ in ring C is a single bond; where $R_{16}$ is a hydrogen atom or methyl group; where ~ indicates the $R_{16}$ group can be in either the $\alpha$ or $\beta$ configuration and where $\rightleftharpoons$ is a single or double bond, must be protected at the C-3 position before reaction with the metalated olefin (VI). The androst-4-ene-3,17-diones (I) are protected as the 3-enol ether (IIa), 3-enamine (IIb) or ketal (IIc).

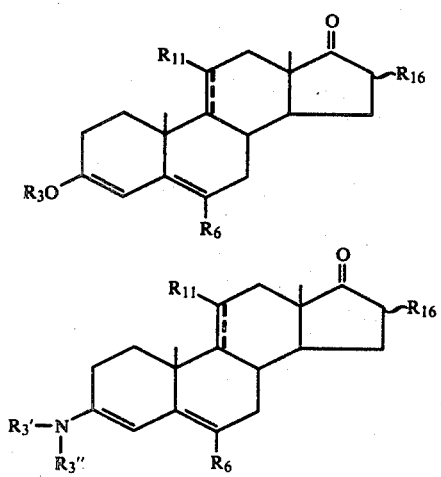

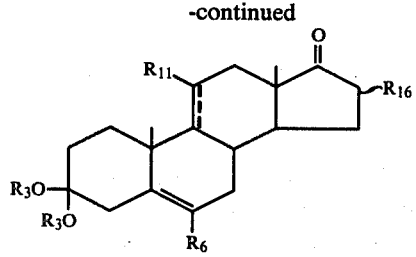

Where $R_3$ is alkyl of 1 thru 5 carbon atoms, with the proviso that with the ketal the $R_3$ groups can be connected to form the ethylene ketal; $R_3'$ and $R_3''$ are the same or different and are alkyl of 1 thru 5 carbon atoms. The enol ethers (IIa) are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The 3-enamines (IIb) are also prepared by methods well known in the art, see U.S. Pat. No. 3,629,298 and Steroid Reactions, supra, page 49–53. The ketals (IIIc) are also prepared by well known methods, see Steroid Reactions, supra, page 11–14. The androsta-1,4-diene-3,17-diones (I) are protected as the 3-dialkylenamine (IId) or ketal (IIe)

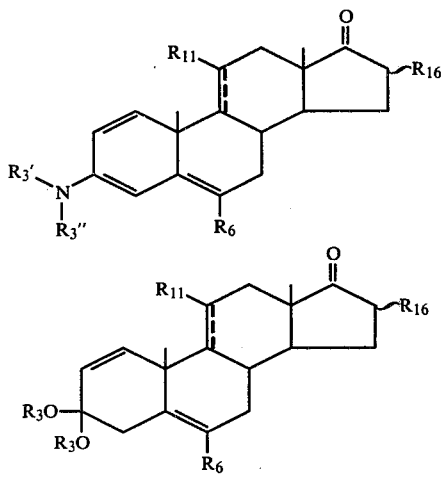

In Chart A, the compound of formula (IIa) can be replaced by either the compound of formula (IIb or IIc) all of which by the process of the present invention will produce the corresponding intermediate compound of the formula (IIIa, IIIb or IIIc), 21-aldehyde (IVa) and 16-unsaturated pregnane (Va). Likewise with the $\Delta^1$ steroids the compound of formula (IId) can be replaced by the compound of formula (IIe) which by the process of the present invention will produce the corresponding intermediate compound of the formula (IIIe), the 21-aldehyde (IVb) and the 16 -unsaturated pregnane (Vb).

When $R_{11}$ is hydroxyl, either $\alpha$ or $\beta$, the hydroxyl group must be protected during the metalated olefin (organo lithium) reaction. The protecting group (TMS) can then be removed by means well known to those skilled in the art.

The protected 17-keto steroids (IIa, IIb or IIc) are reacted with a metalated olefin (VIa and VIb) or (VIb). The metalated olefins (VIa and VIb)

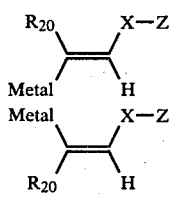

are generated from their corresponding olefins (VIIa and VIIb),

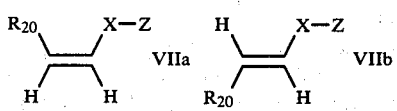

which are well known to those skilled in the art or can readily be prepared from known compounds by methods well known to those skilled in the art, by reaction with a metal-base such as n-butyl lithium, phenyl lithium, methyl lithium and sec-butyl lithium. The preferred metal-base is n-butyl lithium.

Metal includes lithium, sodium, potassium, zinc and magnesium. Lithium is the preferred metal. X is an oxygen or sulfur atom, or $-NR_n-$ where $R_n$ is alkyl of 1 thru 3 carbon atoms. Z is alkyl 1 thru 5 carbon atoms. $R_{20}$ is a fluorine or chlorine atom, $-NR_\alpha R_\beta$ where $R_\alpha$ and $R_\beta$ are the same or different and are a hydrogen atom of alkyl of 1-3 carbon atoms. It is preferred that $R_{20}$ be a chlorine atom.

It is preferred that the metalated olefin be the cis-trans (VIa and VIb) mixture.

The olefin (VIIa and VIIb) can be prepared from the corresponding acetal by reaction with an acid. For example chloroacetaldehyde diethyl acetal is slowly added to a mixture of an acid such as p-TSA in a high boiling organic diluent which has been heated to 200°-250°. The ratio of cis-trans isomers produced is temperature dependent and the optimum temperature for the best ratio of trans to cis isomers is about 230°. When addition is complete the mixture is heated for about another 30 minutes or until the product no longer distills. As the olefin (VII) is formed it distills since its boiling point is considerably less than 200°. The olefin (VII) is distilled into a low boiling organic diluent such as pentane, hexane or SSB which after a bicarbonate wash and drying is removed under reduced pressure to leave an isomeric mixture of olefins (VIIa and VIIb). The isomeric olefins (VIIa and VIIb) can be separated, if so desired, by means well known to those skilled in the art for separating geometrical isomers.

The cis-trans (VIIa and VIIb) or trans (VIIb) olefin in an inert aprotic diluent such as THF, pentane, diethyl ether, hexane, toluene is cooled to $-100°$ to $-20°$, preferably between $-60°$ and $-30°$, more preferably about $-45°$ under an inert atmosphere such as nitrogen. The metal-base is added slowly (dropwise) so as to keep the temperature below $-25°$ preferably below $-40°$. At this temperature the corresponding cis-trans (VIIa and VIIb) or trans (VIIb) metalated olefin is generated in less than 40 minutes, usually in about 15 minutes.

The protected 17-keto steroid (IIa-IIe) is suspended in an inert aprotic diluent such as those listed above or added as the solid. It is preferable if the same diluent be used. The protected 17-keto steroid (IIa-IIe) is cooled to about $-60°$ to $-30°$, preferably to about $-45°$. The metalated olefin (VIa and VIb) or (VIb) and the protected 17-keto steroid (IIa-11d) are then contacted. The metalated olefin (VIa and VIb) or (VIb) can be added to the protected steroid (IIa-IIe) or the protected steroid can be added to the metalated olefin. In order to avoid side reactions it is important to premix the olefin (VIIa and VIIb) or (VIIb) with the metal-base prior to the contacting with the protected 17-keto steroid (IIa—IIe).

The protected 17-keto steroid (IIa-IIe) and the metalated olefin (VIa and VIb) or (VIb) are mixed at a temperature below $-25°$, preferably about 31 60° to $-35°$. The olefin intermediate (IIIa-IIIe) can be isolated after about 0.5-20 hours, preferably about 3 hours, if it is so desired by quenching the reaction with a suitable quenching agent such as water, $R_{17a}$-W, $(R_{17a}CO)_2O$ or $R_{17a}COM$ where $R_{17a}$ is alkyl of 1 thru 3 carbon atoms, thereby $R_{17}$ is a hydrogen atom, alkyl of 1 thru 3 carbon atoms or an acyl group of 2 thru 4 carbon atoms. M is a chlorine or bromine atom. W is a is a bromine or iodine atom. Preferred quenching agents include methyl iodide, methyl bromide, and ethyl iodide. Most preferred is methyl iodide.

Alternatively and preferably the olefin intermediate (IIIa-IIIe) is not isolated but is hydrolyzed by acid, greater than 1 equivalent being required, preferably about 6 equivalents. The particular acid is not critical, acids such as sulfuric, phosphoric, hydrochloric, acetic, citric, benzoic are all suitable. The reaction mixture is warmed to about 25–50) and stirred until the reaction is complete as measured by TLC. The reaction mixture is worked up by the usual methods and concentrated to give the crude 21-aldehyde (IV). When one starts with the protected Δ⁴-3-keto steroid (IIa–IIc) the 21-aldehyde (IV) produced will obviously be the 21-aldehyde (IVa). Likewise when one practices the process of the present invention beginning with the protected Δ¹,⁴-3-keto steroid (IId or IIe) the 21-aldehyde (IV) produced will be the 21-aldehyde (IVb). The term 21-aldehyde (IV) when used is meant to include and apply to both 21-aldehydes (IVa and IVb) when appropriate. The 21-aldehyde (IV) is crystallized from solvents such as methylene chloride-heptane. When the 17-keto steroid (I) is androst-4,9(II)-diene-3,17-dione and the metalated olefin is trans-2-choro-2-lithio-1-ethoxyethylene or a cis-trans mixture the yield of the 21-aldehyde (IV) for 4 experiments was 85.5, 87.9, 90.4 and 88.0% chemical yield, see Examples 3-6.

The 21-aldehyde (IV) is a mixture of the 2 geometrical isomers

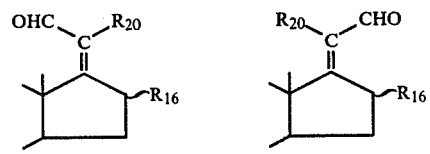

formed in approximately equal amounts. The isomeric 21-aldehydes (IV) can be separated if desired but for the purposes of the present invention it is not necessary and even undesirable to do so since both isomeric 21-aldehydes (IV) are converted to the desired 16-unsaturated pregnane (V).

The term, 20-bromopregna-4,9(II),17(20)-trien-3-one-21-al, as used in both the specification and claims is meant to include both geometrical isomers.

Chart B discloses an alternative, but less preferred, process for producing the 21-aldehyde (IV) which is via an isolatable intermediate (IIIf or IIIg). The isolatable intermediates (IIIf and IIIg) are obtained from (IIIa–IIIc) and (IIId and IIIe) respectively by reaction with a compound such as phosphorous oxychloride (POCl₃) with a co-reagent base such as pyridine at about −45°. The respective products (IIIf and IIIg) can then be transformed to the 21-aldehyde (IV) by reaction with an acid as described above for the compounds (IIIa–IIIc) and (IIId and IIIe).

CHART B

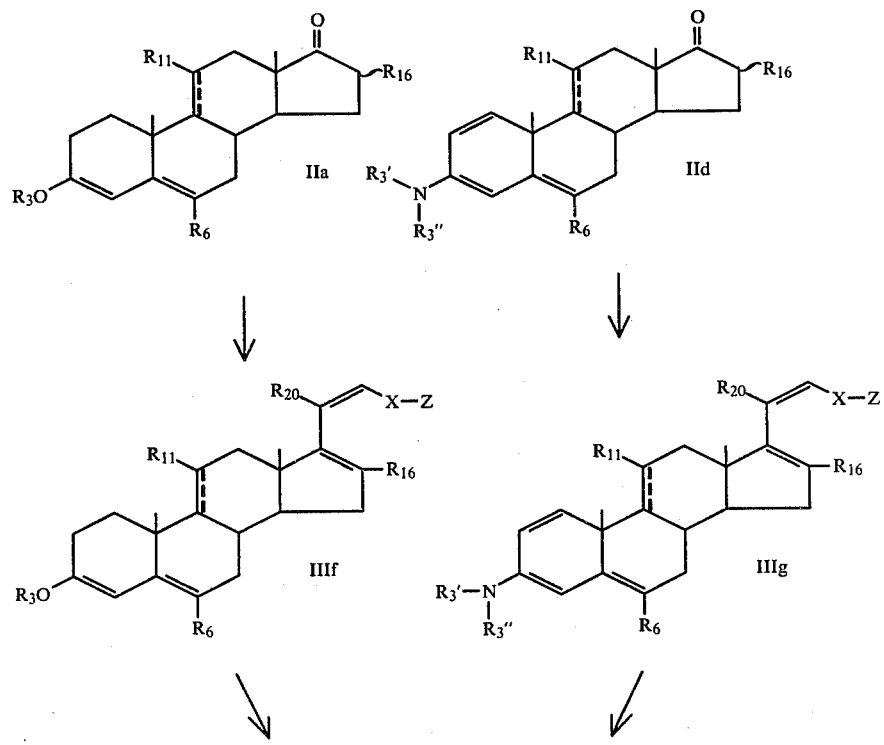

CHART B
-continued

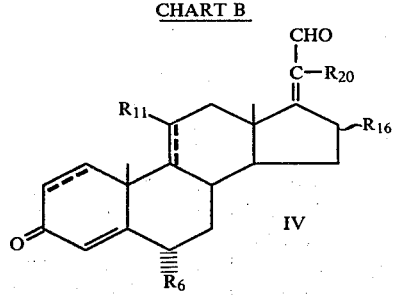

The formulas for the compounds (IIIa–IIIg) all show the double bond at $C_{20}$ to be trans. When the metalated olefin (VI) is a cis-trans mixture then the double bond at $C_{20}$ of the compounds (IIIa–IIIg) should be a mixture of cis and trans. When the metalated olefin (VI) is the trans isomer then the double bond at $C_{20}$ will of course be trans. In the specification, examples and claims when the cis-trans nature of the $C_{20}$ bond is not specified it will have the same geometry as that of the starting metalated olefin compound (VI) as is well known to those skilled in the art. Whether the $C_{20\text{-}21}$ double bond is cis-trans or just trans in the compounds of formula (III) is not of great importance inasmuch as upon acid hydrolysis they are both converted to the identical 21-aldehyde (IV) which in itself exists in two geometrically isomeric forms. It is understood that the formula for the 21-aldehyde (IV) is meant to represent both isomeric 21-aldehydes. Again, it is not critical as to which 21-aldehyde isomer is obtained inasmuch as both are converted to the identical 16-unsaturated pregnane (V).

During the acid hydrolysis of the compounds of formulas (IIIa–IIIe) to the 21-aldehyde (IV) the protecting group is removed from these five compounds regardless of whether they were protected an ether, enamine or ketal and the desired 21-aldehyde (IV) is obtained as the 3-keto compound.

In the case of enamines (IIIb, IIId and IIIg) if the reaction medium is a little too acidic it should be neutralized with a base to a pH of approximately 3 to 4 which is preferable for removal of the enamine protecting group.

The 21-aldehydes (IV) are converted to the corresponding 16-unsaturated pregnane (V) by reaction with an alkali metal or alkaline earth metal salt of a carboxylic acid of the formula $R_{21}COOH$ in a polar organic solvent. When the 21-aldehyde (IV) is saturated at $C_1$ (IVa) the 16-unsaturated pregnane (V) obtained is the corresponding $C_1$ saturated 16-unsaturated pregnane (Va). When the 21-aldehyde (IV) is the $\Delta^{1,4}$-compound (IVb) the corresponding $\Delta^{1,4}$-16-unsaturated pregnane (Vb) is obtained. The term 16-unsaturated pregnane (V) is meant to include and apply to both 16-unsaturated pregnanes (Va and Vb) when appropriate. $R_{21}$ is alkyl of 1 thru 5 carbon atoms or phenyl. Suitable salts of these acids include, for example, potassium acetate, sodium acetate, magnesium propionate, calcium butyrate and sodium benzoate. Suitable organic diluents for the reaction include DMF, pyridine, THF, DMAC and the like. It is preferred the organic diluent be DMF and the salt be sodium or potassium acetate. The reaction is conducted in the range of 50°–200°, preferably 100°–150° depending on the particular 21-aldehyde (IV), the salt and the diluent and is usually complete in 4–8 hrs. The process is best performed by using crystalline 21-aldehyde (IV) and adding it slowly to a mixture of DMF and acetate at about 120° under nitrogen. The reaction is monitored by TLC, ethyl acetate-hexane (1:1). When the reaction is complete it is cooled and an organic diluent such as toluene is added. The mixture is extracted twice with sodium chloride (5%) and back washed twice with an organic diluent. The organic diluents are combined, dried and concentrated under reduced pressure to give the 16-unsaturated pregnanes (V).

20-Bromopregna-4,9(11),17(20)-trien-3-one-21-al is converted to the corresponding 16-unsaturated pregnane (Va) by the same process as the compounds of formula (Va).

The olefins (IIIa–IIIg) and the 21-aldehydes (IV) are useful intermediates in the production of the 16-unsaturated pregnanes (V).

The 16-unsaturated pregnanes (V) are useful in the synthesis of a number of aniti-inflammatory cortical steroids. If the substituents $R_6$ and $R_{16}$ are hydrogen and in the final product it is desired they not be hydrogen they can be transformed to the desired substituent within the scope of their definition by means well known to those skilled in the art. If unsaturation is not present at C-1 and it is desired, the compound may be dehydrogenated by known means. If substitution at $R_6 R_{16}$ or unsaturation A C-1 or C-9(11) is desired these substituents may be added to the 17-keto steroid (I) before beginning the synthesis thereby having the desired substitution in the molecule when the 16-unsaturated pregnane (V) is obtained.

In particular, 21-acetoxypregna-4,9(11),16-triene-3,20-dione (V) is a very useful intermediate in the synthesis of commercially valuable steroids. It is well known to those skilled in the art that the 16-unsaturated pregnanes (V) can be transformed to 16α-hydroxy, 16α-methyl and 16β-methyl steroids.

For example both U.S. Pat. No. 2,864,834 and J. Am. Chem. Soc. 78, 5693 (1956) describe procedures for transforming 21-acetoxy-pregna-4,9(11), 16-triene-3,20-dione (V) to 9α-fluoro-11β, 16α, 17α,21-tetrahydroxy-pregna-1,4-diene-3,20-dione (triamcinolone). J. S. Mills et al. in J. Am. Chem. Soc. 82, 3399 (1960) describe a method by which 21-acetoxypregna-4,9(11),16-triene-3,20-dione (V) could readily be transformed to 6α,9α-difluoro-11β,16α,17α,21-tetrahydroxypregna-1,4-diene-3,20-dione 16,17-acetonide (fluorocinolone acetonide).

U.S. Pat. No. 3,923,985 describes a process for the introduction of a 16α-methyl group into 21-acetoxy-pregna-1,4,9(11),16-tetraene-3,20-dione (V) to give 21-acetoxy-16α-methylpregna-1,4,9(11)-triene-3,20-dione which by methods well known to those skilled in the art can be converted to 16α-methyl steroids such as 6α-fluoro-11β,17α,21-trihydroxy-16α-methylpregna-1,4-diene-3,20-dione (paramethasone) and its 21-acetate; 9α-fluoro-11β,17α,21-trihydroxy-16α-methylpregna-1,4-diene-3,20-dione (dexamethasone) and 6α,9α-difluoro-11β,17α,21-trihydroxy-16α-methylpregna-1,4-diene-3,20-dione (flumethasone).

The definitions and explanations below are for the terms as used throughout the entire patent application including both the specification and claims.

All temperatures are in degrees Centigrade.
TLC refers to thin-layer chromatography.
GC refers to gas chromatography.
THF refers to tetrahydrofuran.
TMS refers to trimethylsilyl.
DMSO refers to dimethylsulfoxide.
DMF refers to dimethylformamide.
SSB refers to an isomeric mixture of hexanes.
DMAC refers to dimethylacetamide.
p-TSA refers to p-toluenesulfonic acid.
IR refers to infrared spectroscopy.
UV refers to ultraviolet spectroscopy.
PMR refers to proton magnetic resonance spectroscopy, chemical shifts are reported in ppm (ε) downfield from TMS.

When solvent pairs are used, the ratio of solvents used are volume/volume (v/v).

$R_3$ is alkyl of 1 thru 5 carbon atoms with the proviso that with the ketal the $R_3$ groups can be connected to form the ethylene ketal.

$R_6$ is a hydrogen or fluorine atom or methyl group.

$R_{11}$ is a hydrogen atom, α-$OR_{11a}$ or β $OR_{11a}$ with the proviso that when $R_{11}$ is —$OR_{11a}$≕in ring C is a single bond.

$R_{11a}$ is a hydrogen atom or TMS.

$R_{16}$ is a hydrogen atom or methyl group.

$R_{17}$ is a hydrogen atom, alkyl of 1 thru 3 carbon atoms or an acyl group of 2 thru 4 carbon atoms.

$R_{17a}$ is alkyl of 1 thru 3 carbon atoms.

$R_{20}$ is a fluorine or chlorine atom or —$NR_\alpha R_\beta$.

$R_{21}$ is alkyl of 1 thru 5 carbon atoms or phenyl.

$R_3'$ and $R_3''$ are the same or different and are alkyl of 1 thru 5 carbon atoms.

$R_\alpha$ and $R_\beta$ are the same or different and are alkyl of 1 thru 3 carbon atoms.

$R_n$ is alkyl of 1 thru 3 carbon atoms.

M is a chlorine or bromine atom.

W is a bromine or iodine atom.

X is an oxygen or sulfur atom or —$NR_n$—.

Z is alkyl of 1 thru 5 carbon atoms.

Metal is lithium, sodium, potassium, zinc and magnesium.

∼ indicates the $R_{16}$ group can be in either the α or β configuration.

≕ is a single or double bond.

EXAMPLES

The invention may be more fully understood from the following examples which are illustrative of the process and compounds of the present invention but are not to be construed as limiting.

Preparation 1—2-Chloro-1-ethoxyethylene (VII)

p-TSA is added to hexadecane and heated to 230°. Chloroacetaldehyde diethyl acetal is added slowly with stirring. The isomeric 2-chloro-1-ethoxyethylenes (VIIa and VIIb) distill and are collected in a receiver containing aqueous bicarbonate and hexane. When the reaction is complete, the organic phase is separated and the hexane removed under reduced pressure to give a mixture of cis and trans 2-chloro-1-ethoxyethylene (VIIa and VIIb).

Preparation 2—2-Chloro-1-ethoxyethylene (VII)

Hexadecane (16 ml.), p-TSA (367 mg.) and tetraethylorthosilicate (1.8 ml.) are stirred at 230°±5°. Chloroacetaldehyde diethyl acetal (50 g.) is added slowly (about 0.2 ml./min.). Heating is continued and the mixture is permitted to distill 0.5 hours after all the acetal has been added until no more material distilled. The distillate is separated, re-extracted with potassium bicarbonate (10%, 10 ml.) and back washed with pentane (15 ml.). The pentane phases are combined, dried over magnesium sulfate-potassium carbonate and filtered. The filtrate is heated at 70°–80° until no more pentane distills leaving an isomeric mixture of the title compounds.

Preparation 3—Trans-2-chloro-1-ethoxyethylene (VIIb)

The cis-trans mixture of 2-chloro-1-ethoxyethylene (VIIa and VIIb, Preparations 1 and 2) is subjected to distillation. The title compound distills at 100° leaving the cis isomer which distills at 116°.

Preparation 4—Androsta-1,3,5,9(11)-tetraene-17-one 3-diethylenamine (IId)

Following the general procedure of U.S. Pat. No. 3,629,298 in particular Example E and making non-critical variations but substituting androsta-1,4,9(11)-triene-3,17-dione for androsta-4,9(11)-diene-3,17-dione the title compound is obtained.

EXAMPLE 1

20-Chloropregna-4,9(11),17(20)-triene-3-one-21-al (IVa)

THF (7.5 ml.) and trans-2-chlorovinyl ethyl ether (VIIb, Preparation 3, 215 mg.) are cooled to −45°. n-Butyllithium (1.40 ml.) is added dropwise over 5 minutes so the temperature remains below −40°. The mixture is stirred 15 minutes and 3-hydroxyandrosta-3,5,9(11)-triene-17-one 3-methyl ether (IIa, U.S. Pat. No. 3,516,991, 453 mg.) is added all at once and stirred for 3–3.5 hours at −45°. The mixture is warmed to 0°. Hydrochloric acid (6N, 1.5 ml.) is added and the two-phase mixture stirred at 20°–25°. When the reaction is complete as monitored by TLC, hexane-ethyl acetate (80:20), a potassium carbonate solution is added to neutralize the mixture. After neutralization the 2 phases are separated, and the organic phase is concentrated to a solid. GC analysis of the solid material shows the 2 isomeric 21-aldehydes (IV) which are obtained in 91.2% yield (chemical) are present in about 1:1.

EXAMPLE 2

21-Hydroxypregna-4,9(11),16-triene-3,20-dione-21-acetate (Va)

A mixture of 20-chloropregna-4,9(11),17(20)-triene-3-one 21-al (IVa, Example 1, 333 mg.) in DMF (3.5 ml.) is stirred with anhydrous potassium acetate (300 mg.) and acetic anhydride (25 μl.) at 106° for 1 hour. Toluene (25 ml.) is added. The toluene phase is extracted with water (2×25 ml.) and back extracted with toluene (2×10 ml.). The combined toluene samples are stirred (30 minutes) with activated charcoal (30 mg.), filtered and concentrated to give the title compound.

EXAMPLE 3

20-Chloropregna-4,9(11),17(20)-triene-3-one-21-al (IVa)

Anhydrous THF (60 ml.) and 2-chloro-1-ethoxyethylene (VIIa and VIIb, Preparation 1, 12.0 ml., 12.29 g.) are cooled to −45° under nitrogen. n-Butyllithium (72 mmole) is added dropwise over 15 minutes keeping the temperature below −40°. This is followed by a 4 ml. hexane rinse. The mixture is stirred for about 15 minutes. Precooled 3-hydroxyandrosta-3,5,9(11)-triene-17-one 3-methyl ether (IIa, 18.0 g.) is added all at once and rinsed in with 4 ml. of hexane. The mixture is stirred 3 hours, the cooling stopped and hydrochloric acid (6N, 12 ml.) is added. The mixture is warmed to about 38° and placed under reduced pressure to remove most of the THF and hexane. Another portion of hydrochloric acid (6N, 50 ml.) and methylene chloride (60 ml.) is added and stirred for 3.25 hours at 35°. The phases are separated and the aqueous phase is extracted with methylene chloride (2×25 ml.). The organic phases are washed with potassium carbonate (5%, 50 ml.). The combined methylene chloride extracts are dried and concentrated to give the crude chloroaldehyde (IV).

The solid is redissolved in methylene chloride (36 ml.) and heptane (45 ml.) is added. The mixture is seeded and heptane (170 ml.) is added dropwise over about 1.5 hours. The slurry is stirred for 1 hour at 20°–25°, 1 hour at 0°, filtered and the solids washed with heptane-methylene chloride (95:5) and pentane (2×25 ml.) and dried to give an isomeric mixture of the title compound, 17.805 g. (85.5% chemical yield). PMR (CDCl$_3$) 1.02, 1.1, 1.37, 5.55, 5.75, 9.7 and 9.9 $\delta$.

Following the general procedure of Example 3 and making non-critical variations, Examples 4, 5, and 6 give the following yields (chemical)

| Example | Yield (Chemical) % |
|---------|--------------------|
| 4 | 87.9 |
| 5 | 90.4 |
| 6 | 88.0 |

EXAMPLE 7

21-Hydroxypregna-4,9(11),16-triene-3,20-dione-21-acetate (Va)

Anhydrous sodium acetate (5.8 g.) and DMF are stirred and heated at 120° under nitrogen. Crystalline 20-chloropregna-4,9(11),17(20)-triene-3-one-21-al (IVa, Example 3, 12 g.) is added by adding 2 gm. every 20 minutes. The mixture is stirred for 90 minutes at 120°, the reaction cooled and toluene (100 ml.) is added. The mixture is extracted with sodium chloride (5%, 2×100 ml.) and backwashed with toluene (2×20 ml.). The toluene phase is dried over magnesium sulfate and concentrated under reduced pressure to give the title compound, m.p. 120°–124°, PMR (CDCl$_3$) 0.89, 1.35, 2.18, 4.95, 5.55, 5.72 and 6.74 $\delta$.

EXAMPLE 8

20-Chloro-3,17β,21-trihydroxypregna-3,5,9(11),20-tetraene 3,17-dimethyl-21-ethyl ether (IIIa)

THF (30 ml.) and 2-chloro-1-ethoxyethylene (VIIa, 4.42 mmoles and VIIb 39.78 mmoles) are stirred at −45°. n-Butyl lithium (36.75 mmole) is added dropwise over 15 minutes and the mixture is stirred another 15 minutes. Pre-cooled 3-hydroxyandrosta-3,5,9(11)-triene-17-one 3-methyl ether (IIa, 9.08 g.) is added and the mixture stirred for 3 hours at −45°, kept 24 hours at −18° and THF (37.2 g.) is added.

To 5.6 ml. of the above mixture methyl iodide (0.3 ml.) is added and the mixture is stirred at 60°. When the reaction is complete as measured by TLC, hexane-ethyl acetate (75:25) is added and it is worked up by adding potassium carbonate (20%, 20 ml.) and ethyl acetate (20 ml.) to which triethylamine (0.2 ml.) had been added. The organic phase is separated, dried and concentrated to give the title compound. PMR (CDCl$_3$) 0.89, 1.12, 3.20, 3.55, 3.8, 5.1, 5.2, 5.45 and 6.6 $\delta$; mass spectroscopy 418, 403 and 369.

EXAMPLE 9

20-Chloropregna-4,9(11),17(20)-triene-3-one-21-al (IVa)

THF (7.5 ml.) and 20-chloro-3,17β,21-trihydroxypregna-3,5,9(11),20-tetraene 3,17-dimethyl-21-ethyl ether (IIIa, Example 8, 500 mg.) is cooled to 0°. Hydrochloric acid (6N, 1.5 ml.) is added and the two-phase mixture stirred at 20°–25° until the reaction is complete as monitored by TLC, hexane-ethyl acetate (80:20). The reaction mixture is then worked up according to Example 1 to give an isomeric mixture (about 1:1) of the title compound.

EXAMPLE 10

20-Chloropregna-1,4,9(11),17(20)-tetraene-3-one-21-al (IVb)

Following the general procedure of Example 1 and making non-critical variations but starting with androsta-1,3,5,9(11)-tetraene-17-one 3-diethylenamine (IId, Preparation 4) instead of 3-hydroxyandrosta-3,5,9(11)-triene-17-one 3-methyl ether the title compound is obtained.

EXAMPLE 11

20-Chloropregna-1,4,9 (11),17(20)-tetraene-3-one-21-al (IVb)

Following the general procedure of Example 3 and making non-critical variations but starting with androsta-1,3,5,9(11)-tetraene-17-one 3-diethylenamine (IId, Preparation 4) instead of 3-hydroxyandrosta-3,5,9(11)-triene-17-one 3-methyl ether the title compound is obtained.

EXAMPLE 12

20-Chloro-17β,21-dihydroxypregna-1,3,5,9(11),20-pentaene 17-methyl-21-ethyl ether 3-diethylenamine (IIId)

Following the general procedure of Example 8 and making non-critical variations but starting with androsta-1,3,5,9(11)-tetraene-17-one 3-diethylenamine (IId, Preparation 4) instead of 3-hydroxyandrosta-3,5,9(11)-triene-17-one 3-methyl ether the title compound is obtained.

EXAMPLE 13

20-Chloropregna-1,4,9(11),17(20)-triene-3-one-21-al (IVb)

Following the general procedure of Example 9 and making non-critical variations but starting with 20-chloro-17β,21-dihydroxypregna-1,3,5,9(11),20-pentane 17-methyl-21-ethyl ether 3-diethylenamine (IIId, Example 12) instead of 20-chloro-3,17β,21-trihydroxypregna-3,5,9(11),20-tetraene 3,17-dimethyl-21-ethyl ether the title compound is obtained.

EXAMPLE 14

20-Chloro-3,21-dihydroxypregna-3,5,9(11),16,20-pentaene 3-methyl-21-ethyl ether (IIIf)

THF (15 ml.) and trans-2-chloro-1-ethoxyethylene (VIb) are cooled to −45° and n-butyl lithium (12.0 ml.) is added dropwise maintaining the temperature below −40°. The mixture is stirred 20 minutes and precooled 3-hydroxyandrosta-3,5,9(11)-triene-17-one 3-methyl ether (IIa, 4.50 g.) is added and stirred for 3 hours at −45°. Phosphorus oxychloride (1.65 ml., precooled to −45°) is added and stirred for 5 minutes. The cooling is stopped and triethylamine (5.5 ml.) is added dropwise over 10 minutes, stirring is continued until the mixture reaches room temperature. The mixture is worked up by adding ethyl acetate (100 ml.) and extracting with potassium carbonate (20%, 3×50 ml.) and back extracting with ethyl acetate (50 ml.). The ethyl acetate is dried and concentrated under reduced pressure to yield the title compound. PMR (CDCl$_3$) 0.95, 1.19, 1.36, 3.61, 4.05, 5.18, 5.28, 5.5, 5.95, and 6.62 δ; mass spectroscopy 400, 386 and 371.

EXAMPLE 15

20-Chloropregna-4,9(11),17(20)-triene-3-one-21-al (IVa)

Following the general procedure of Example 9 and making non-critical variations but starting with 20-chloro-3,21-dihydroxypregna-3,5,9(11),16,20-pentaene 3-methyl-21-ethyl ether (IIIf, Example 14) instead of 20-chloro-3,17β,21-trihydroxypregna-3,5,9(11),20-tetraene 3,17-dimethyl-21-ethyl ether the title compound is obtained.

EXAMPLE 16

20-Chloro-21-hydroxypregna-1,3,5,9(11),16,20-hexaene 21-ethyl ether 3-diethylenamine (IIIg)

Following the general procedure of Example 14 and making non-critical variations but starting with androsta-1,3,5,9(11)-tetraene-17-one 3-diethylenamine (IId) instead of 3-hydroxyandrosta-3,5,9(11)-triene-17-one 3-methyl ether (IIa) the title compound is obtained.

EXAMPLE 17

20-Chloropregna-1,4,9(11),17(20)-tetraene-3-one-21-al (IVb)

Following the general procedure of Example 9 and making non-critical variations but starting with 20-chloro-21-hydroxypregna-1,3,5,9(11),16,20-hexaene 21-ethyl ether 3-diethylenamine (IIIg, Example 16) the title compound is obtained.

EXAMPLE 18

20-Chloropregna-4,17(20)-diene-3-one-21-al (VIa)

Following the general procedure of Example 1 or 3 and making non-critical variations but starting with 3-hydroxyandrosta-3,5-diene-17-one 3-methyl ether [IIa, J. Org. Chem. 26, 3924 (1961) at page 3928] the title compound is obtained.

EXAMPLE 19

20-Chloro-3,17β,21-trihydroxypregna-3,5,20-triene 3,17-dimethyl-21-ethyl ether (IIIa)

Following the general procedure of Example 8 and making non-critical variations but starting with 3-hydroxyandrosta-3,5-diene-17-one 3-methyl ether (IIa) the title compound is obtained.

EXAMPLE 20

20-Chloro-3,17β,21-trihydroxypregna-3,5,9(11),20-tetraene 3-methyl-21-ethyl ether (IIIa)

THF (5.0 ml.) and trans-2-chlorovinyl ethyl ether (VIIb, Preparation 3, 0.75 ml.) are cooled to −45°. n-Butyl lithium (4.0 ml.) is added dropwise over 15–20 minutes while keeping the temperature below −40°. The mixture is stirred 15 minutes and precooled 3-hydroxyandrosta-3,5,9(11)-triene-17-one 3-methyl ether (IIa, 1.51 g.) is added. After stirring 3 hours at −45° the reaction mixture is poured with stirring into a mixture of methylene chloride (50 ml.) and potassium bicarbonate solution (10%, 50 ml.) at 20°–25°. Upon work up the title compound is obtained. PMR (CDCl$_3$) 0.90, 1.18, 1.30, 3.60, 3.88, 5.20, 5.25, 5.55 and 6.41 δ.

EXAMPLE 21

20-Bromopregna-4,9(11),17(20)-trien-3-one-21-al

Following the general procedure of Example 1 and making non-critical variations but substituting trans-2-bromo-1-ethoxyethylene for trans-2-chloro-1-ethoxyethylene the title compound is obtained, m.p. 145°–149° (decomposition); PMR (CDCl$_3$) 1.05, 1.14, 1.38, 5.55, 5.77, 9.63 and 9.75 δ; IR (CHCl$_3$) 1667, 1610 and 1592 cm$^{-1}$; UV (methanol) 242 mμ; mass spectrum 390, 388, 375, 373 and 309.

EXAMPLE 22

21-Hydroxypregna-4,9(11),16-triene-3,20-dione-21-acetate (Va)

Following the general procedure of Examples 2 and 7 and making non-critical variations but substituting 20-bromopregna-4,9(11),17(20)-trien-3-one-21-al for 20-chloropregna-4,9 11),17(20)-trien-3-one-21-al the title compound is obtained.

We claim:

1. A process for preparation of a compound of the formula:

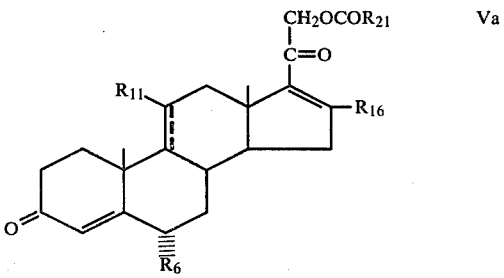

where R$_6$ is a hydrogen or fluorine atom or methyl group; where R$_{11}$ is a hydrogen atom, α—OR$_{11a}$ or β—OR$_{11a}$; where R$_{11a}$ is a hydrogen atom or TMS with the proviso that when R$_{11}$ is —OR$_{11a}$, == in ring C is a single bond; where R$_{16}$ is a hydrogen atom or methyl group; where R$_{21}$ is alkyl of 1 thru 5 carbon atoms or phenyl and where ≕ is a single or double bond which comprises:

(1) reacting a compound of the formula:

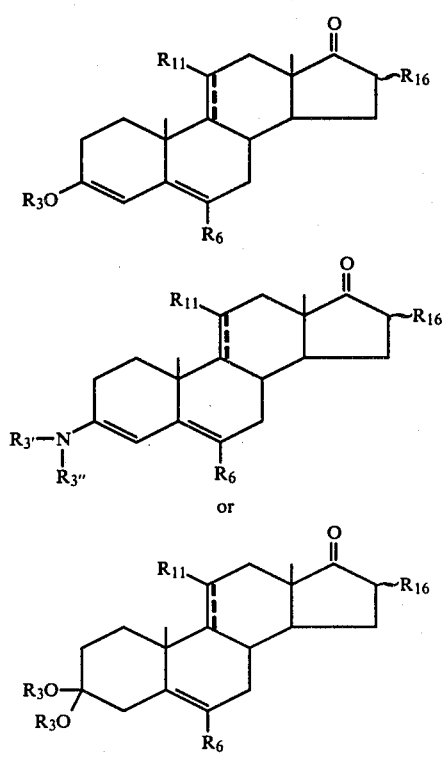

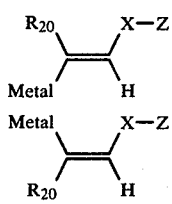

where $R_3$ is alkyl of 1 thru 5 carbon atoms; with the proviso that with the ketal the $R_3$ groups can be connected to form the ethylene ketal; where $R_{3'}$ and $R_{3''}$ are the same or different and are alkyl of 1 thru 5 carbon atoms; and where ∼ indicates $R_{16}$ is in either the α or β configuration, with a metalated olefin selected from the group consisting of a cis-trans mixture (VIa and VIb) or trans (VIb) compounds of the formula:

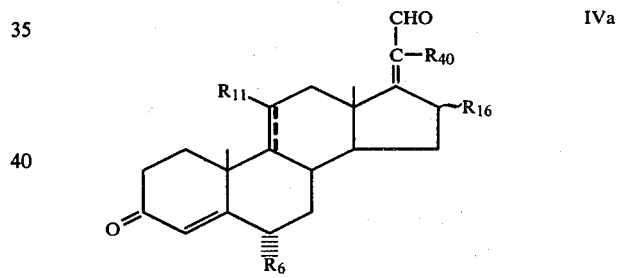

where X is an oxygen or sulfur atom or —$NR_n$—; where $R_n$ is alkyl or 1 thru 3 carbon atoms; where Z is alkyl of 1 thru 5 carbon atoms; where Metal is selected from the group consisting of lithium, sodium, potassium, zinc, and magnesium and where $R_{20}$ is selected from the group consisting of a fluorine or chlorine atom or —$NR_\alpha R_\beta$ where $R_\alpha$ and $R_\beta$ are the same or different and are alkyl of 1 thru 3 carbon atoms; to form a compound of the formula:

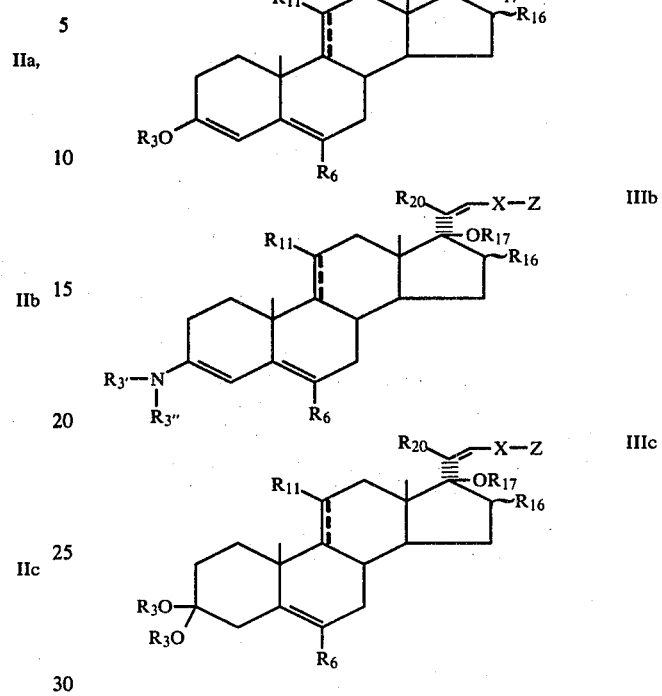

(2) acid hydrolysis of the olefin (IIIa–IIIc) to form a 21-aldehyde (IVa) of the formula:

![IVa structure]

and (3) reaction of the 21-aldehyde (IVa) with a compound of the formula $R_{21}CO_2\ominus$ in an aprotic diluent.

2. A process according to claim 1 where $R_6$ is a hydrogen or fluorine atom.

3. A process according to claim 2 where the 16-unsaturated pregnane (Va) is 21-hydroxypregna-4,16-diene-3,20-dione 21-acetate.

4. A process according to claim 1 where ≕ in the C ring of the compound of formula Va is a double bond.

5. A process according to claim 4 where the 16-unsaturated pregnane (Va) is 21-hydroxypregna-4,9(11), 16-triene-3,20-dione 21-acetate.

6. A process according to claim 1 where the metalated olefin is the cis-trans mixture (VIa and VIb).

7. A process according to claim 6 where the metalated olefin is 2-chloro-2-lithio-1-ethoxyethylene.

8. A process according to claim 1 where the metalated olefin is the trans isomer (VIb).

9. A process according to claim 8 where the metalated olefin is trans-2-chloro-2-lithio-1-ethoxyethylene.

10. A process according to claim 1 where in the metalated olefin the Metal is lithium and $R_{20}$ is a chlorine atom.

11. A process according to claim 1 where step (1) is performed at less than or equal to $-25°$.

12. A process according to claim 1 where $R_{21}CO_2^\ominus$ is acetate.

13. A process according to claim 1 where the aprotic diluent is selected from the group consisting of DMF or DMSO.

14. A process for preparation of 21-hydroxypregna-4,9(11), 16-triene-3,20-dione 21-acetate which comprises:
   (1) reacting 3-hydroxyandrosta-3,5,9(11)-triene-17-one 3-methyl ether with a cis-trans mixture of 2-chloro-2-lithio-1-ethoxyethylene to give cis and trans 20chloro-3,17$\beta$,21-trihydroxy-17$\alpha$-pregna-3,5,9(11),20-tetraene 3-methyl-21-ethyl ether;
   (2) hydrolysis of the product of step (1) with acid to give 20-chloropregna-4,9(11), 17(20)-trien-3-one-21-al (IVa) and
   (3) reacting the product of step (2) with acetate in DMF.

15. A process for preparation of 21-hydroxypregna-4,9(11),16-triene-3,20-dione 21-acetate which comprises:
   (1) reacting 3-hydroxyandrosta-3,5,9(11)-triene-17-one 3-methyl ether with trans-2-chloro-2-lithio-1-ethoxyethylene to give trans 20-chloro-3,17$\beta$,21-trihydroxy-17$\alpha$-pregna-3,5,9(11),20-tetraene 3-methyl-21-ethyl ether;
   (2) hydrolysis of the product of step (1) with acid to give 20-chloropregna-4,9(11), 17(20)trien-3-one-21-al (IVa) and
   (3) reacting the product of step (2) with acetate in DMF.

16. A process for the preparation of both geometrical isomers at $C_{20}$ of a compound of the formula:

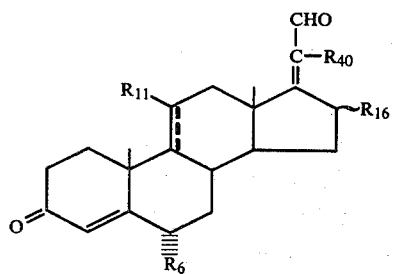

which comprises:
(1) reacting a compound of the formula:

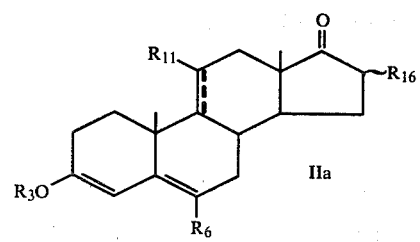

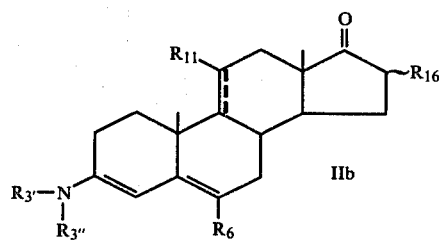

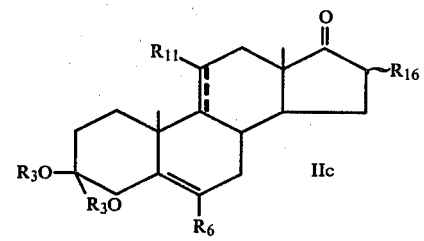

with a metalated olefin selected from the group consisting of a cis-trans mixture (VIa and VIb) or trans (VIb) compound of the formula:

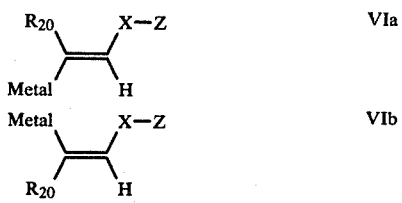

and (2) acid hydrolysis where $R_3$, $R_3'$, $R_3''$, $R_6$, $R_{11}$, $R_{16}$, $R_{20}$, X, Z, Metal, ~ and $\doteq$ are defined in claim 1.

17. A process according to claim 16 where $R_6$ is a hydrogen or fluorine atom.

18. A process according to claim 17 where the 21-aldehyde (IVa) is 20-chloropregna-4,16-diene-3-one-21-al.

19. A process according to claim 16 where $\doteq$ in the C ring is a double bond.

20. A process according to claim 19 where the 21-aldehyde (IVa) is 20-chloropregna-4,9(11), 16-triene-3-one-21-al.

21. A process according to claim 16 where the metalated olefin is the cis-trans mixture (VIa and VIb).

22. A process according to claim 21 where the metalated olefin is 2-chloro-2-lithio-1-ethoxyethylene.

23. A process according to claim 16 where the metalated olefin is the trans isomer (VIb).

24. A process according to claim 23 where the metalated olefin is trans-2-chloro-2-lithio-1-ethoxyethylene.

25. A process according to claim 16 where in the metalated olefin the Metal is lithium and $R_{20}$ is a chlorine atom.

26. A process according to claim 16 where step (I) is performed at less than or equal to $-25°$.

27. A process for the preparation of a compound of the formula:

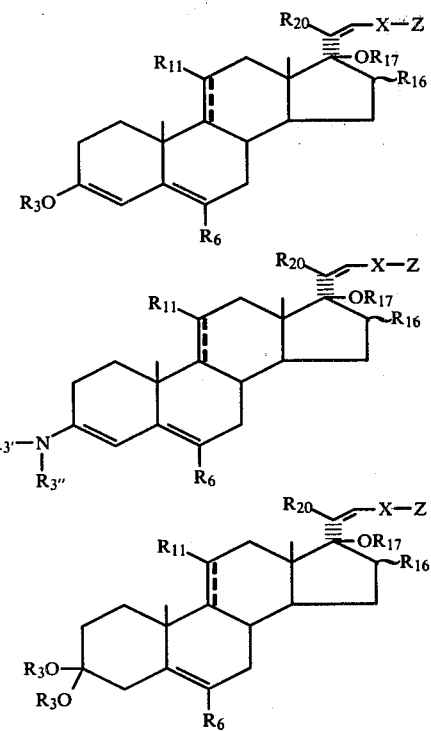

and the cis C<sub>20-21</sub> isomer thereof where R$_{17}$ is a hydrogen atom, alkyl of 1 thru 3 carbon atoms or an acyl group of 2 thru 5 carbon atoms which comprises:

(1) reacting the corresponding C-3 protected compound of the formula:

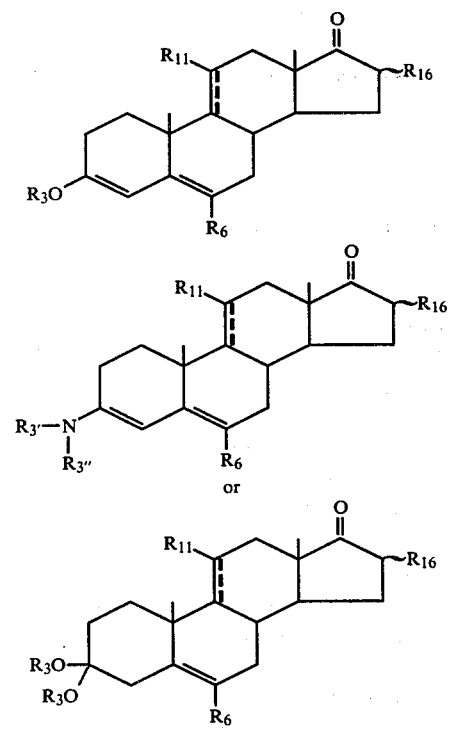

with a metalated olefin selected from the group consisting of a cis-trans mixture (VIa and VIb) or trans (VIb) compound of the formula:

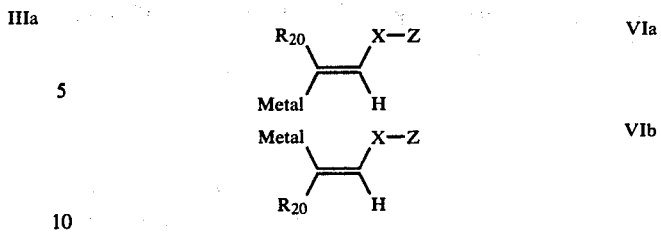

and (2) quenching the reaction with a compound of the formula R$_{17a}$-W, (R$_{17a}$CO)$_2$O, R$_{17a}$COM or water; where R$_{17a}$ is alkyl of 1 thru 3 carbon atoms; where W is a bromine or iodine atom where M is a chlorine or bromine atom; where R$_3$, R$_6$, R$_{11}$, R$_{16}$, R$_{20}$, X, Z, ~, ═ and Metal are defined in claim 1.

28. A process according to claim 27 where R$_6$ is a hydrogen or fluorine atom.

29. A process according to claim 28 where the steroid (IIIa) is 20-chloro-3,17β,21-trihydroxypregna-3,5,20-triene-3,17-dimethyl-21-ethyl ether.

30. A process according to claim 27 where the ═ in the C ring of the compound IIIa, IIIb or IIIc is a double bond.

31. A process according to claim 30 where the steroid (IIIa) is 20-chloro-3,17β,20-trihydroxypregna-3,5,9(11),20-tetraene 3,17-dimethyl-21-ethyl ether.

32. A process according to claim 27 where the metalated olefin is the cis-trans mixture (VIa and VIb).

33. A process according to claim 32 where the metalated olefin is 2-chloro-2-lithio-1-ethoxyethylene.

34. A process according to claim 27 where the metalated olefin is the trans isomer (IVb).

35. A process according to claim 34 where the metalated olefin is trans-2-chloro-2-lithio-1-ethoxyethylene.

36. A process according to claim 27 where in the metalated olefin the Metal is lithium and R$_{20}$ is a chlorine atom.

37. A process according to claim 27 where the step (I) is performed at less than or equal to −25°.

38. A process for the preparation of both geometrical isomers at C$_{20}$ of a compound of the formula:

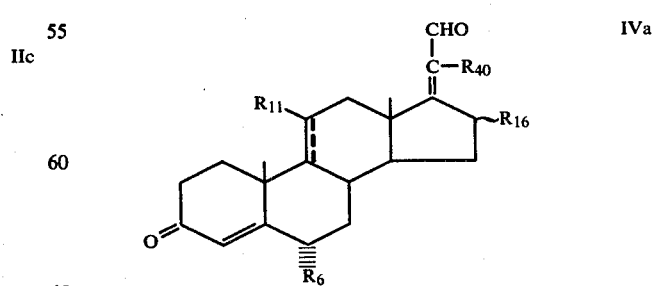

which comprises acid hydrolysis of a compound of the formula:

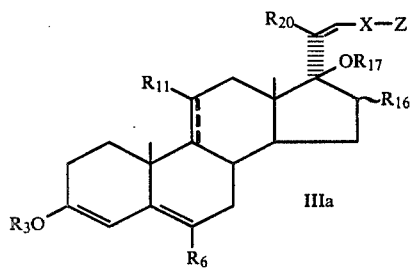

IIIa

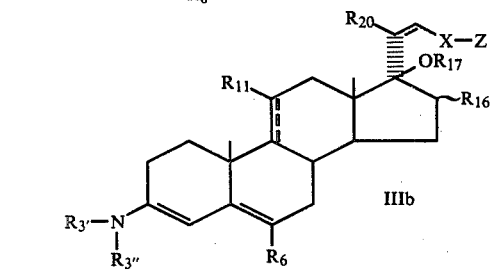

IIIb or

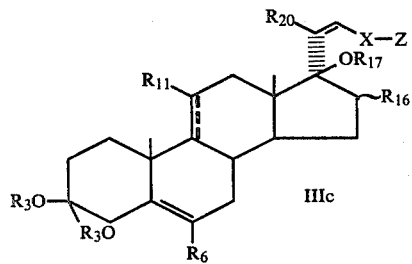

IIIc or the cis $C_{20-21}$ isomer thereof where $R_3$, $R_3'$, $R_3''$, $R_6$, $R_{11}$, $R_{16}$, $R_{20}$, X, Z, $\sim$ and $\doteq$ a are defined in claim 1 and where $R_{17}$ is defined in claim 27.

39. A process according to claim 38 where the compound of formula (IVa) is 20-chloropregna-4,9(11),17(20)-triene- 3-one-21-al.

40. A process for preparation of a compound of the formula:

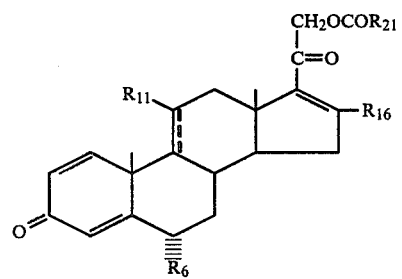

Vb which comprises:
(1) reacting a compound of the formula:

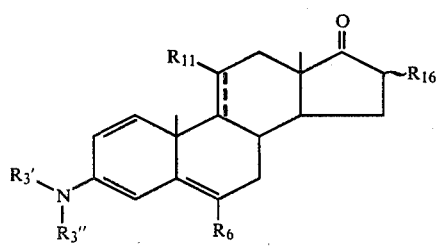

IId

-continued or

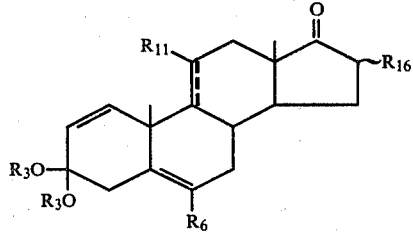

IIe with a metalated olefin selected from the group consisting of a cis-trans mixture (VIa and VIb) or trans (VIb) compounds of the formula:

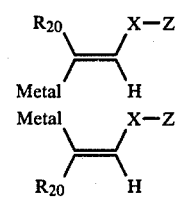 VIa

 VIb to give a compound of the formula:

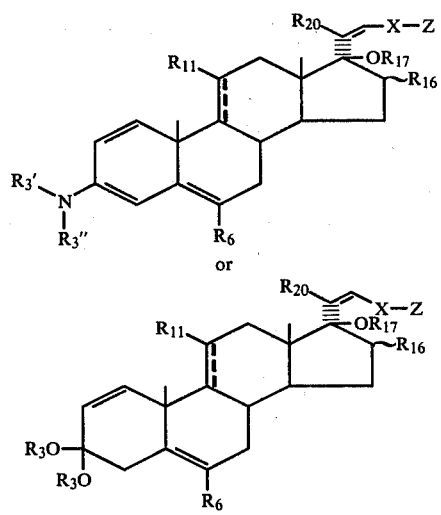

IIId or

IIIe (2) acid hydrolysis of the olefin (IIId or IIIe) to give a 21-aldehyde (IVb) of the formula:

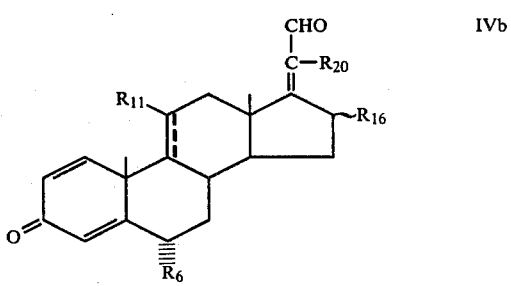

IVb and
(3) reaction of the 21-aldehyde (IVb) with a compound of the formula $R_{21}CO_2^{\ominus}$ in an aprotic diluent where $R_3$, $R_3'$, $R_3''$, $R_6$, $R_{11}$, $R_{16}$, $R_{21}$, $\sim$ and $\doteq$ are defined in claim 1.

41. A process according to claim 40 where $R_6$ is a hydrogen or fluorine atom.

42. A process according to claim 40 where ≕ in the C ring of compound Vb is a double bond.

43. A process according to claim 42 where the 16-unsaturated steroid (Vb) is 21-hydroxypregna-1,4,9(11),16-tetraene-3,20-dione 21-acetate.

44. A process according to claim 40 where the metalated olefin is the cis-trans mixture (VIa and VIb).

45. A process according to claim 44 where the metalated olefin is 2-chloro-2-lithio-1-ethoxyethylene.

46. A process according to claim 40 where the metalated olefin is the trans isomer (VIb).

47. A process according to claim 46 where the metalated olefin is trans-2-chloro-2-lithio-3-ethoxyethylene.

48. A process according to claim 40 where in the metalated olefin the Metal is lithium and $R_{20}$ is a chlorine atom.

49. A process according to claim 40 where step 1) is performed at less than or equal to $-25°$.

50. A process according to claim 40 where $R_{21}CO_2^{\ominus}$ is acetate.

51. A process according to claim 40 where the aprotic diluent is selected from the group consisting of DMF or DMSO.

52. A process for preparation of 21-hydroxypregna-1,4,9(11),16-tetraene-3,20-dione 21-acetate which comprises:

(1) reacting androsta-1,3,5,9(11)-tetraene-17-one-3-diethylenamine with a cis-trans mixture of 2-chloro-2-lithio-1-ethoxyethylene to give a compound of the formula:

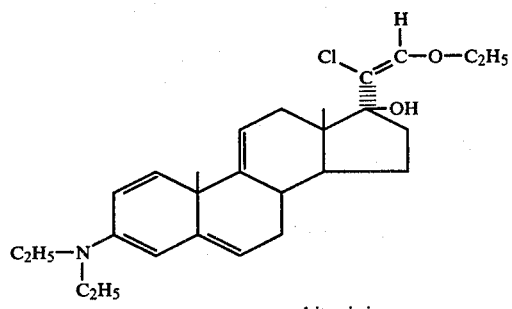

and its cis isomer (2) hydrolysis of the product of step (1) with acid to give 20-chloropregna 1,4,9(11),17(20)-tetraen-3-one-21-al (IVb) and (3) reacting the product of step (2) with acetate in DMF.

53. A process for preparation of 21-hydroxypregna-1,4,9(11),16-tetraene-3,20-dione 21-acetate which comprises:

(1) reacting androsta-1,3,5,9(11)-tetraene-17-one-3-diethylenamine with trans-2-chloro-2-lithio-1-ethoxyethylene to give a compound of the formula:

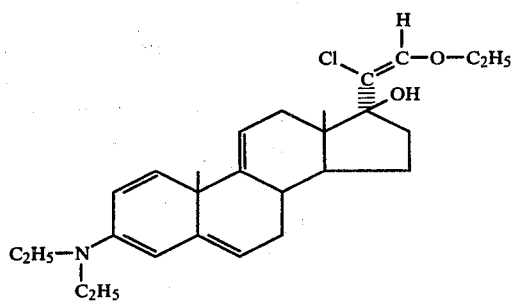

(2) hydrolysis of the product of step (1) with acid to give 20-chloropregna-1,4,9(11),17(20)-tetraen-3-one-21-al (IVb) and (3) reacting the product of step (2) with acetate in DMF, 54. A process for the preparation of both geometrical isomers at $C_{20}$ of a compound of the formula:

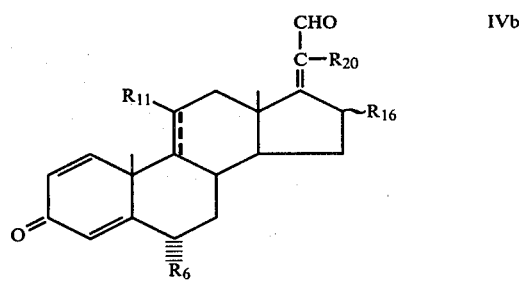

IVb which comprises:

(1) reacting a compound of the formula:

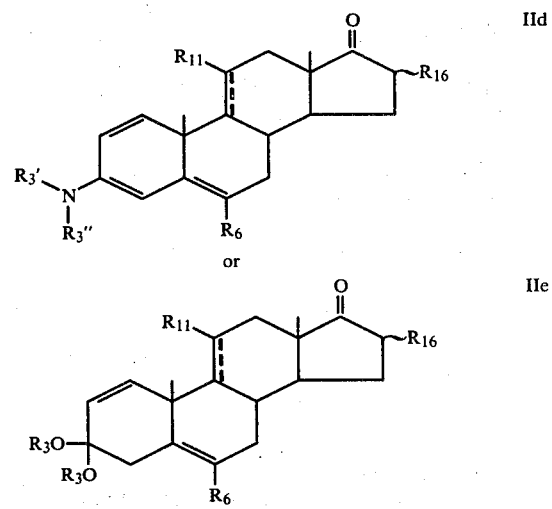

IId or

IIe with a metalated olefin selected from the group consisting of a cis-trans mixture (VIa and VIb) or trans (VIb) compound of the formula:

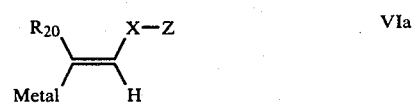

VIa

-continued

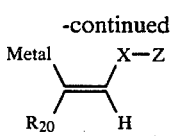  VIb and (2) acid hydrolysis where $R_3$, $R_3'$, $R_3''$, $R_6$, $R_{11}$, $R_{16}$, $R_{20}$, X, Z, Metal, $\sim$ and $=$ are defined in claim 1.

55. A process according to claim 54 where $R_6$ is a hydrogen or fluorine atom.

56. A process according to claim 54 where $=$ in the C ring is a double bond.

57. A process according to claim 56 where the 21-aldehyde (IVb) is 20-chloropregna-1,4,9(11),17(20)-tetraene-3-one 21-al.

58. A process according to claim 54 where the metalated olefin is the cis-trans mixture (VIa and VIb).

59. A process according to claim 58 where the metalated olefin is 2-chloro-2-lithio-1-ethoxyethylene.

60. A process according to claim 54 where the metalated olefin is the trans isomer (IVb).

61. A process according to claim 60 where the metalated olefin is trans-2-chloro-2-lithio-3-ethoxyethylene.

62. A process according to claim 54 where the Metal is lithium and $R_{20}$ is a chlorine atom.

63. A process according to claim 54 where step (1) is performed at less than or equal to $-25°$.

64. A process for the preparation of a compound of the formula:

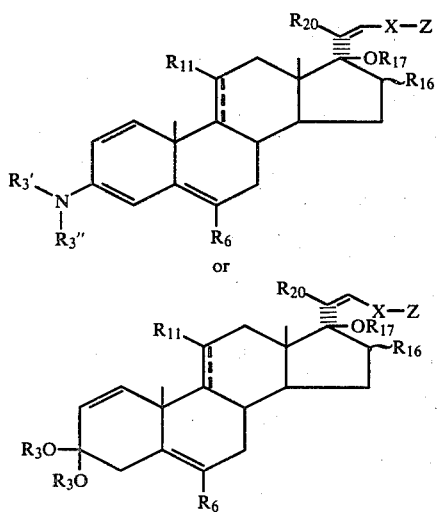

and the cis $C_{20-21}$ isomer thereof which comprises:
(1) reacting the corresponding $C_3$ protected compound of the formula:

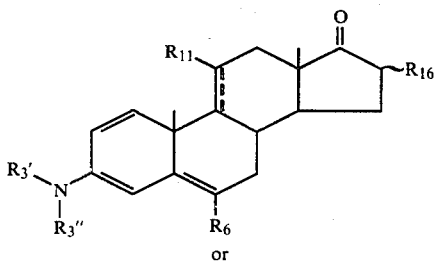

or

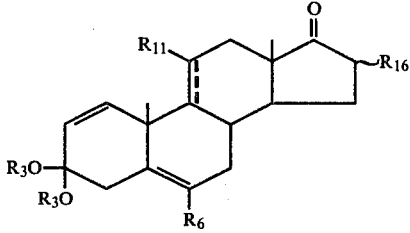  IIe with a metalated olefin selected from the group consisting of a cis-trans mixture (VIa and VIb) or trans (VIb) compound of the formula:

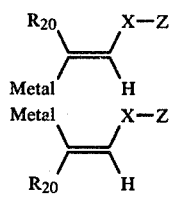

and (2) quenching the reaction with a compound of the formula $R_{17a}$-W, $(R_{17a}CO)_2O$, $R_{17a}COM$; where $R_{17a}$ is alkyl of 1 thru 3 carbon atoms; where $R_3$, $R_3'$, $R_3''$, $R_6$, $R_{11}$, $R_{16}$, $R_{20}$, X, Z, $\sim$, $=$ and Metal are defined in claim 1, and where $R_{17}$, M and W were defined in claim 27.

65. A process according to claim 64 where $R_6$ is a hydrogen or fluorine atom.

66. A process according to claim 64 where the $=$ in the C ring is a double bond.

67. A process according to claim 66 where the steroid (IIId) is 20-chloro-17β,21-dihydroxypregna-1,3,5,9(11),20-pentaene 17-methyl-21-ethyl ether 3-diethylenamine.

68. A process according to claim 64 where the metalated olefin is the cis-trans mixture (VIa and VIb).

69. A process according to claim 68 where the metalated olefin is 2-chloro-2-lithio-1-ethoxyethylene.

70. A process according to claim 64 where the metalated olefin is the trans isomer (VIb).

71. A process according to claim 70 where the metalated olefin is trans-2-chloro-2-lithio-1-ethoxyethylene.

72. A process according to claim 64 where the Metal is lithium and $R_{20}$ is a chlorine atom.

73. A process according to claim 64 where the step (1) is performed at less than or equal to $-25°$.

74. A process for the preparation of both geometrical isomers at $C_{20}$ of a compound of the formula:

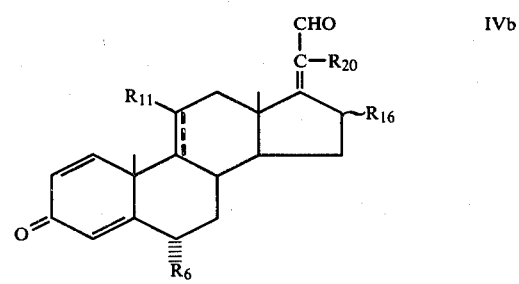

which comprises acid hydrolysis of a compound of the formula:

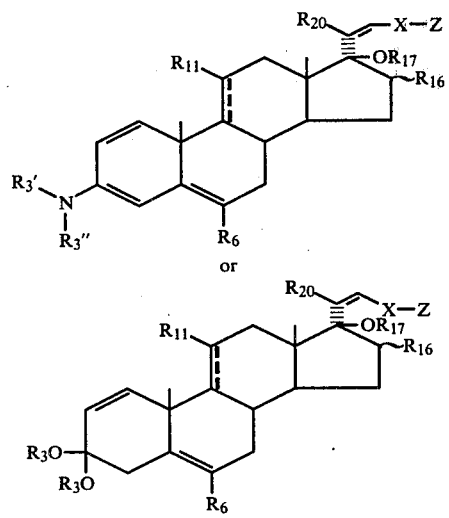

or the cis $C_{20-21}$ isomer thereof where $R_3$, $R_3'$, $R_3''$, $R_6$, $R_{11}$, $R_{16}$, $R_{20}$, X, Z, ~, and == are defined in claim 1 and where $R_{17}$ is defined in claim 27.

75. A process according to claim 74 where the compound of formula (IVb) is 20-chloropregna-1,4,9(11),17(20)-tetraene-3-one-21-al.

76. A compound of the formula:

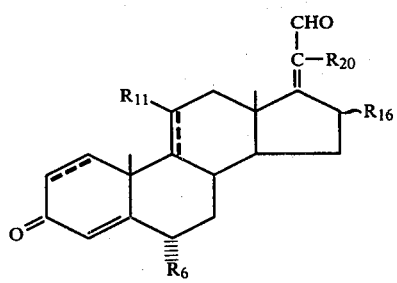

and the geometrical isomer thereof at $C_{20}$ where $R_6$, $R_{11}$, $R_{16}$, $R_{20}$, ~ and == are defined in claim 1.

77. A compound according to claim 76 where === in ring A is a single bond.

78. A compound according to claim 76 where $R_6$ is a hydrogen or fluorine atom.

79. A compound according to claim 76 where $R_{20}$ is a chlorine atom.

80. A compound according to claim 76 where == in ring A is a double bond.

81. A compound according to claim 80 where $R_{20}$ is a chloring atom.

82. a compound according to claim 81 which is 20-chloropregna-1,4,9(11),17(20)-tetraene-3-one-21-al.

83. A compound according to claim 76 where == in ring C is a double bond.

84. A compound according to claim 83 where == in ring A is a single bond.

85. A compound according to claim 84 where $R_6$ is a hydrogen or fluorine atom.

86. A compound according to claim 85 where $R_{20}$ is a chlorine atom.

87. A compound according to claim 86 which is 20-chloropregna-4,9(11),17(20)-triene-3-one-21-al.

88. A compound of the formula:

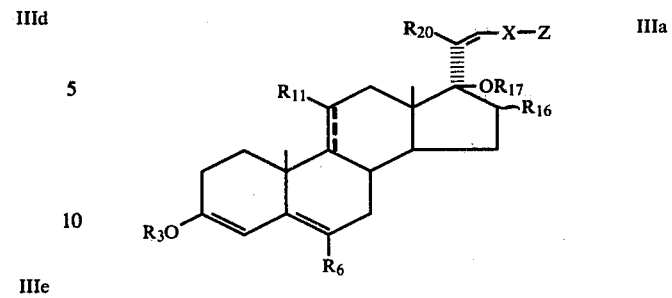

and the $C_{20-21}$ cis isomer thereof where $R_3$, $R_{11}$, $R_6$, $R_{16}$, $R_{20}$, X, Z, ~, and == are defined in claim 1 and where $R_{17}$ is defined in claim 27.

89. A compound according to claim 88 where $R_3$ is methyl or ethyl, $R_{20}$ is a chlorine atom and X is an oxygen atom.

90. A compound according to claim 89 which is 20-chloro-3,17β,21-trihydroxypregna-3,5,9(11),20-tetraene 3,17-dimethyl-21-ethyl ether.

91. A compound according to claim 89 which is 20-chloro-3,17β,21-trihydroxypregna-3,5,9(11),20-tetraene 3-methyl-21-ethyl ether.

92. A compound according to claim 89 which is 20-chloro-3,17β,21-trihydroxypregna-3,5,20-triene 3,17-dimethyl-21-ethyl ether.

93. A compound of the formula:

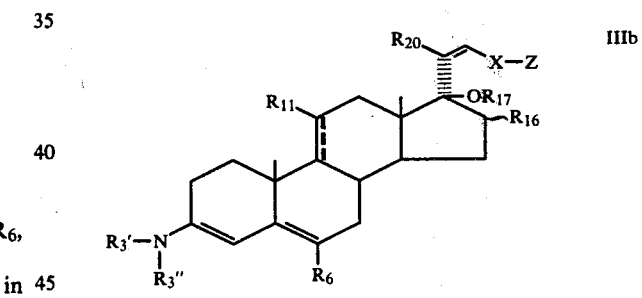

and the $C_{20-21}$ cis isomer thereof where $R_3'$, $R_3''$, $R_6$, $R_{11}$, $R_{16}$, $R_{20}$, X, Z, ~ and == are defined in claim 1 and where $R_{17}$ is defined in claim 27.

94. A compound of the formula:

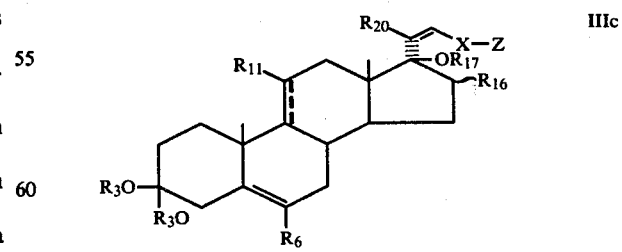

and the $C_{20-21}$ cis isomer thereof where $R_3$, $R_6$, $R_{11}$, $R_{16}$, $R_{20}$, X, Z, ~ and == are defined in claim 1 and where $R_{17}$ is defined in claim 27.

95. A compound of the formula:

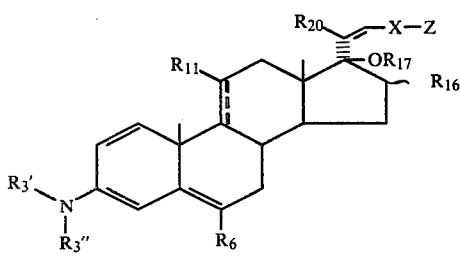 IIId and the $C_{20-21}$ cis isomer thereof where $R_3'$, $R_3''$, $R_6$, $R_{11}$, $R_{16}$, $R_{20}$, X, Z, ~ and $=$ are defined in claim 1; and where $R_{17}$ is defined in claim 27.

96. A compound according to claim 95 where $R_3'$ and $R_3''$ are methyl or ethyl, $R_{20}$ is a chlorine atom, and X is an oxygen atom.

97. A compound according to claim 96 which is 20-chloro-17β,21-dihydroxypregna-1,3,5,9(11),20-pentaene 17-methyl-21-ethyl ether 3-diethylenamine.

98. A compound of the formula:

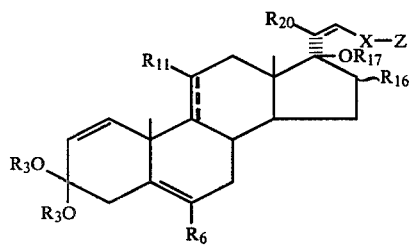 IIIe and the $C_{20-21}$ cis isomer thereof where $R_3$, $R_6$, $R_{11}$, $R_{16}$, $R_{20}$, X, Z, ~ and $=$ are defined in claim 1 and where $R_{17}$ is defined in claim 27.

99. A compound of the formula:

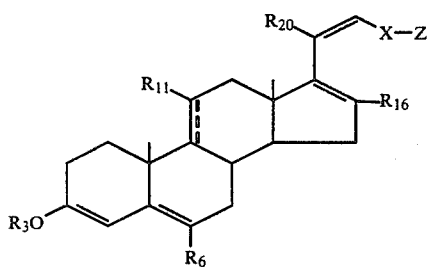 IIIf and the $C_{20-21}$ isomer thereof where $R_3$, $R_6$, $R_{11}$, $R_{16}$, $R_{20}$, X and Z are defined in claim 1.

100. A compound according to claim 99 where $R_3$ is methyl or ethyl, $R_{20}$ is a chlorine atom and X is an oxygen atom.

101. A compound according to claim 100 which is 20-chloro--3,21-dihydroxypregna-3,5,9(11),16,20-pentaene 3-methyl-21-ethyl ether.

102. A compound of the formula:

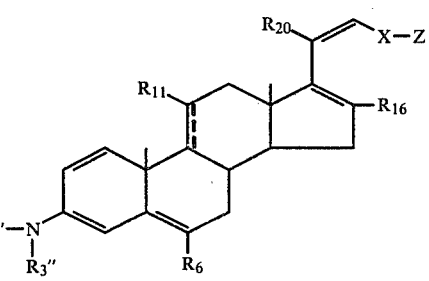 IIIg and the $C_{20-21}$ isomer thereof where $R_3'$, $R_3''$, $R_6$, $R_{11}$, $R_{16}$, $R_{20}$, X and Z are defined in claim 1.

103. A compound according to claim 102 where $R_3'$ and $R_3''$ are methyl or ethyl, $R_{20}$ is a chlorine atom and X is an oxygen atom.

104. A compound according to claim 103 which is 20-chloro-21-hydroxypregna-1,3,5,9(11),16,20-hexaene-21-ethyl ether 3-diethylenamine.

105. A process for the preparation of 20-chloropregna-4,9(11),17(20)-triene-3-one-21-al which comprises:
(1) reacting 3-hydroxyandrosta-3,5,9(11)-triene-17-one 3-methyl ether with a cis-trans mixture of 2-chloro-2-lithio-1-ethoxyethylene to give cis and trans 20-chloro-3,17β,21-trihydroxy-17α-pregna-3,5,9(11),20-tetraene 3-methyl-21-ethyl ether and
(2) hydrolysis of the product of step (1) with acid.

106. A process for the preparation of 20-chloropregna-4,9(11),17(20)-triene-3-one-21-al which comprises:
(1) reacting 3-hydroxyandrosta-3,5,9(11)-triene-17-one 3-methyl ether with trans-2-chloro-2-lithio-1-ethoxyethylene trans 20-chloro-3,17β,21-trihydroxy-17α-pregna-3,5,9(11),20-tetraene 3-methyl-21-ethyl ether and
(2) hydrolysis of the product of step (1) with acid.

107. 20-Bromopregna-4,9(11),17(20)-trien-3-one-al.

108. A process for the preparation of a compound of the formula:

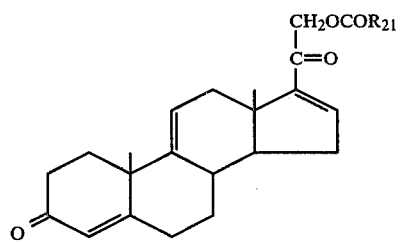 Vc which comprises reacting 20-bromopregna-4,9(11),17(20)-trien-3-one-21-al with a compound of the formula $R_{21}CO_2^{\ominus}$ in an aprotic diluent where $R_{21}$ is defined in claim 1.

109. A process according to claim 108 where $R_{21}$ is methyl.

110. A process according to claim 108 where the aprotic diluent is selected from the group consisting of DMF or DMSO.

111. A process for the preparation of a compound of the formula:

which comprises reacting a compound of the formula:

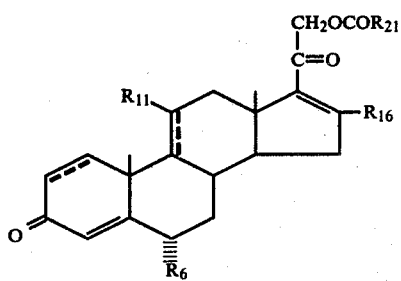

with a compound of the formula $R_{21}CO_2^{\ominus}$ in an aprotic diluent where $R_{21}$ is defined in claim 1.

112. A process according to claim 111 where the compound of formula V is a compound of formula Va.

113. A process according to claim 111 where the compound of formula V is a compound of formula Vb.

114. A process according to claim 111 where $R_{21}$ is methyl.

115. A process according to claim 111 where the aprotic diluent is selected from the group consisting of DMF or DMSO.

116. A process according to claim 115 where the aprotic diluent is DMF.

117. A process according to claim 111 where the compound of formula (V) is 21-hydroxypregna-4,9(11),16-trien-3,20-dione 21-acetate.

118. A process for the preparation of 21-hydroxypregna-4,9(11),16-triene-3,20-dione 21-acetate which comprises reacting 20-chloropregna-4,9(11),17(20)-trien-3-one-21-al with acetate in DMF.

* * * * *

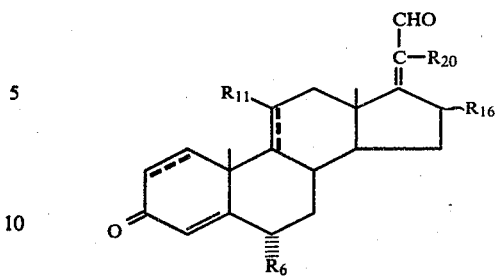

UNITED STATES PATENT AND TRADEMARK OFFICE
CERTIFICATE OF CORRECTION

PATENT NO. : 4,216,159
DATED : August 5, 1980
INVENTOR(S) : Edward J. Hessler and Verlan H. VanRheenen It is certified that error appears in the above—identified patent and that said Letters Patent is hereby corrected as shown below:

Column 3, line 48:
Column 24, line 35:
Column 25, line 46:
Column 28, line 55:

"$\begin{array}{c}\text{CHO}\\|\\\text{C-R}_{40}\\\|\end{array}$" should read $-- \begin{array}{c}\text{CHO}\\|\\\text{C-R}_{20}\\\|\end{array} --$ Column 4, line 38:
Column 6, line 2:
Column 12, lines 56-57:

"$R_{17\alpha}$-W, $(R_{17\alpha}CO)_2O$, $R_{17\alpha}COM$" should read $--R_{17a}$-W, $(R_{17a}CO)_2O$, $R_{17a}COM--$.

Column 9, lines 40-41:
Column 17, lines 32-33:
Column 22, lines 64-65:

"$\alpha$-$OR_{11\alpha}$ or $\beta$-$OR_{11\alpha}$, ...$R_{11\alpha}$" should read $--\alpha$-$OR_{11a}$ or $\beta$-$OR_{11a}$, ...$R_{11a}--$.

Column 9, line 42: "-$OR_{11\alpha}$," should read -- -$OR_{11a}$, --.
Column 10, line 54: "Where" should read -- where -- (no new paragraph).
Column 12, line 42: "(IIa-IId)" should read -- (IIa-IId) --.
Column 12, line 52: "about 31 60° to -35°" should read -- about -60° to -35° --
Column 13, line 10: "(IId or IIe)" should read -- (IId or IIe) --.
Column 13, line 16: "4,9(II)-" should read -- 4,9(11)- --.
Column 13, line 19: "4experiments" should read -- 4 experiments --.
Column 14, line 15: "4,9(II)-" should read -- 4,9(11)- --.

Column 16, line 29: "formula (Va)" should read -- formula (IVa) --.
Column 16, line 34: "aniti-inflammatory" should read -- anti-inflammatory --.
Column 16, line 42: "$R_6R_{16}$ or unsaturation A C-1" should read --$R_6$, $R_{16}$ or unsaturation at C-1 --.
Column 16, line 62: "(flurocinolone" should read -- (fluocinolone --.
Column 17, line 24: "ppm ($\epsilon$)" should read -- ppm ($\delta$) --.
Column 17, line 35: "$R_{11\alpha}$" should read -- $R_{11a}$ --.
Column 17, line 39: "$R_{17\alpha}$" should read -- $R_{17a}$ --.
Column 25, line 19: "20chloro" should read -- 20-chloro --.
Column 25, line 37: "17(20trien-" should read -- 17(20)-trien- --.

UNITED STATES PATENT AND TRADEMARK OFFICE
CERTIFICATE OF CORRECTION

PATENT NO. : 4,216,159
DATED : August 5, 1980
INVENTOR(S) : Edward J. Hessler and Verlan H. VanRheenen It is certified that error appears in the above—identified patent and that said Letters Patent is hereby corrected as shown below:

Column 29, line 37: "--a are" should read -- --- are --.
Column 30, line 1: "or" should not be there.
Column 30, line 38: "or" should not be there.

Column 35, line 55: "a compound" should read -- A compound --.
Column 37, lines 64-66: (Spacing is confusing.)

Signed and Sealed this

Twenty-third Day of December 1980

[SEAL]

Attest:

SIDNEY A. DIAMOND

Attesting Officer

Commissioner of Patents and Trademarks